United States Patent
Bokil et al.

(10) Patent No.: US 11,602,635 B2
(45) Date of Patent: Mar. 14, 2023

(54) SYSTEMS AND METHODS FOR STIMULATION-RELATED VOLUME ANALYSIS OF THERAPEUTIC EFFECTS AND OTHER CLINICAL INDICATIONS

(71) Applicant: Boston Scientific Neuromodulation Corporation, Valencia, CA (US)

(72) Inventors: Hemant Bokil, Santa Monica, CA (US); Stephen Carcieri, Los Angeles, CA (US); Keith R. Carlton, Boston, MA (US); Michael A. Moffitt, Solon, OH (US); Peter J. Yoo, Burbank, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1011 days.

(21) Appl. No.: 16/279,785

(22) Filed: Feb. 19, 2019

(65) Prior Publication Data

US 2019/0184175 A1 Jun. 20, 2019

Related U.S. Application Data

(63) Continuation of application No. 14/813,818, filed on Jul. 30, 2015, now Pat. No. 10,272,247.

(60) Provisional application No. 62/031,075, filed on Jul. 30, 2014.

(51) Int. Cl.
*A61N 1/36* (2006.01)
*A61N 1/372* (2006.01)
*G16H 50/50* (2018.01)
*A61N 1/05* (2006.01)

(52) U.S. Cl.
CPC ..... *A61N 1/36128* (2013.01); *A61N 1/37247* (2013.01); *G16H 50/50* (2018.01); *A61N 1/0534* (2013.01); *A61N 1/0551* (2013.01)

(58) Field of Classification Search
None
See application file for complete search history.

(56) References Cited

U.S. PATENT DOCUMENTS

| | | |
|---|---|---|
| 3,999,555 A | 12/1976 | Person |
| 4,144,889 A | 3/1979 | Tyers |
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner |
| 5,651,767 A | 7/1997 | Schulman |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |

(Continued)

FOREIGN PATENT DOCUMENTS

| | | |
|---|---|---|
| EP | 1048320 | 11/2000 |
| EP | 1166819 | 1/2002 |

(Continued)

OTHER PUBLICATIONS

Nowinski, W. L., et al., "Statistical analysis of 168 bilateral subthalamic nucleus implantations by means of the probabilistic functional atlas.", Neurosurgery 57(4 Suppl) (Oct. 2005),319-30.

Obeso, J. A., et al., "Deep-brain stimulation of the subthalamic nucleus or the pars interna of the globus pallidus in Parkinson's disease.", N Engl J Med., 345{131. The Deep-Brain Stimulation for Parkinson's Disease Study Group, (Sep. 27, 2001 ),956-63.

(Continued)

*Primary Examiner* — G Steven Vanni

(74) *Attorney, Agent, or Firm* — Branch Partners PLLC; Bruce E. Black

(57) ABSTRACT

A computer implemented system and method facilitates a cycle of generation, sharing, and refinement of volumes related to stimulation of anatomical tissue, such as brain or spinal cord stimulation. Such volumes can include target stimulation volumes, side effect volumes, and volumes of estimated activation. A computer system and method also facilitates analysis of groups of volumes, including analysis of differences and/or commonalities between different groups of volumes.

20 Claims, 9 Drawing Sheets

(56) References Cited

U.S. PATENT DOCUMENTS

| | | |
|---|---|---|
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows |
| 6,517,480 B1 | 2/2003 | Krass |
| 6,539,263 B1 | 3/2003 | Schiff |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,136,518 B2 | 5/2006 | Griffin et al. |
| 7,058,446 B2 | 6/2006 | Schuler et al. |
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | Dilorenzo |
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,382 B2 | 3/2008 | McIntyre et al. |
| 7,388,974 B2 | 6/2008 | Yanagita |
| 7,437,193 B2 | 10/2008 | Parramon et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,826,902 B2 | 11/2010 | Stone et al. |

(56) References Cited

U.S. PATENT DOCUMENTS

| | | |
|---|---|---|
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,019,439 B2 | 9/2011 | Kuzma et al. |
| 8,175,710 B2 | 5/2012 | He |
| 8,180,601 B2 | 5/2012 | Butson et al. |
| 8,195,300 B2 | 6/2012 | Gliner et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,364,278 B2 | 1/2013 | Pianca et al. |
| 8,429,174 B2 | 4/2013 | Ramani et al. |
| 8,452,415 B2 | 5/2013 | Goetz et al. |
| 8,543,189 B2 | 9/2013 | Paitel et al. |
| 8,606,360 B2 | 12/2013 | Butson et al. |
| 8,620,452 B2 | 12/2013 | King et al. |
| 8,918,184 B1 | 12/2014 | Torgerson et al. |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Ridder |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027514 A1 | 2/2007 | Gerber |
| 2007/0043268 A1 | 2/2007 | Russell |
| 2007/0049817 A1 | 3/2007 | Preiss |
| 2007/0067003 A1 | 3/2007 | Sanchez et al. |
| 2007/0078498 A1 | 4/2007 | Rezai et al. |
| 2007/0083104 A1 | 4/2007 | Butson |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |

(56) References Cited

U.S. PATENT DOCUMENTS

| | | |
|---|---|---|
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0064249 A1 | 3/2010 | Groetken |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kaula et al. |
| 2010/0179562 A1 | 7/2010 | Linker |
| 2010/0324410 A1 | 12/2010 | Paek et al. |
| 2010/0331883 A1 | 12/2010 | Schmitz et al. |
| 2011/0040351 A1 | 2/2011 | Butson et al. |
| 2011/0066407 A1 | 3/2011 | Butson et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0306845 A1 | 12/2011 | Osorio |
| 2011/0306846 A1 | 12/2011 | Osorio |
| 2011/0307032 A1 | 12/2011 | Goetz et al. |
| 2012/0027272 A1 | 2/2012 | Akinyemi et al. |
| 2012/0046715 A1 | 2/2012 | Moffitt et al. |
| 2012/0078106 A1 | 3/2012 | Dentinger et al. |
| 2012/0089205 A1 | 4/2012 | Boyden et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0314924 A1 | 12/2012 | Carlton et al. |
| 2012/0316619 A1 | 12/2012 | Goetz et al. |
| 2013/0039550 A1 | 2/2013 | Blum et al. |
| 2013/0060305 A1 | 3/2013 | Bokil |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2014/0067018 A1 | 3/2014 | Carcieri et al. |
| 2014/0277284 A1 | 9/2014 | Chen et al. |
| 2015/0134031 A1 | 5/2015 | Moffitt et al. |

FOREIGN PATENT DOCUMENTS

| | | |
|---|---|---|
| EP | 1372780 | 1/2004 |
| EP | 1559369 | 8/2005 |
| KR | 20110066460 | 6/2011 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 20071097859 | 8/2007 |
| WO | 20071097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |

OTHER PUBLICATIONS

Butson et al.. "Current Steering to control the volume of tissue activated during deep brain stimulation," vol. 1, No. 1, Dec. 3, 2007, pp. 7-15.

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.

Phillips, M. D., et ai., "Parkinson disease: pattern of functional MR imaging activation during deep brain stimulation of subthalamic nucleus—initial experience", Radiology 239(1). (Apr. 2006),209-16.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al., "Fast and robust multi-atlas segmentation of brain magnetic resonance images," NeuroImage, Academic Press, vol. 49, No. 3, Feb. 1, 2010, pp. 2352-2365.

McIntyre, C. C., et al., "How does deep brain stimulation work? Present understanding and future questions.", J Clin Neurophysioi. 21 (1 ), (Jan.-Feb. 2004),40-50.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

Plaha, P. , et al., "Stimulation of the caudal zona incerta is superior to stimulation of the subthalamic nucleus in improving contralateral parkinsonism.", Brain 129{Pt 7) (Jul. 2006), 1732-4 7.

Rattay, F, "Analysis of models for external stimulation of axons", IEEE Trans. Biomed. Eng. vol. 33 (1986),974-977.

Rattay, F., "Analysis of the electrical excitation of CNS neurons", IEEE Transactions on Biomedical Engineering 45 (6). (Jun. 1998),766-772.

Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.

(56) References Cited

OTHER PUBLICATIONS

Rubinstein, J. T., et al., "Signal coding in cochlear implants: exploiting stochastic effects of electrical stimulation", Ann Otol Rhinol Laryngol Suppl.. 191, (Sep. 2003), 14-9.
Schwan, H.P., et al., "The conductivity of living tissues.", Ann NY Acad Sci., 65(6). (AUQ., 1957),1007-13.
Taylor, R. S., et al., "Spinal cord stimulation for chronic back and leg pain and failed back surgery syndrome: a systematic review and analysis of prognostic factors", Spine 30(1 ). (Jan. 1, 2005), 152-60.
Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.
Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.
Geddes, L. A., et al., "The specific resistance of biological material—a compendium of data for the biomedical engineer and physiologist.", Med Biol Ena. 5(3). (May 1967),271-93.
Gimsa, J., et al., "Choosing electrodes for deep brain stimulation experiments-electrochemical considerations.", J Neurosci Methods, 142(2), (Mar. 30, 2005),251-65.
Vidailhet, M. , et al., "Bilateral deep-brain stimulation of the globus pallidus in primary generalized dystonia", N Engl J Med. 352(5) (Feb. 3, 2005),459-67.
Izad, Oliver, "Computationally Efficient Method in Predicating Axonal Excitation," Dissertation for Master Degree, Department of Biomedical Engineering, Case Western Reserve University, May 2009.
Jaccard, Paul, "Elude comparative de la distribution florale dans une portion odes Aples et des Jura," Bulletin de la Societe Vaudoise des Sciences Naturelles (1901), 37:547-579.
Dice, Lee R., "Measures of the Amount of Ecologic Association Between Species," Ecology 26(3) (1945): 297-302, doi 10.2307/1932409, http://jstor.org/stable/1932409.
Rand, WM., "Objective criteria for the evaluation of clustering methods," Journal of the American Statistical Association (American Statistical Association) 66 (336) (1971 ): 846-850, doi: 10.2307/2284239, http://jstor.org/stabie/2284239.
Hubert, Lawrence et al., "Comparing partitions," Journal of Classification 2(1) (1985): 193-218, doi:10.1007/BF01908075.
Cover, T.M. et al., "Elements of information theory," (1991) John Wiley & Sons, New York, NY.
Meila, Marina, "Comparing Clusterings by the Variation of Information," Learning Theory and Kernel Machines (2003): 173-187.
Viola, P., et al., "Alignment by maximization of mutual information", International Journal of Com outer Vision 24(2). ( 1997), 137-154.
Butson et al. "StimExplorer: Deep Brain Stimulation Parameter Selection Software System," Acta Neurochirugica, Jan. 1, 2007, vol. 97, No. 2, pp. 569-574.
Butson et al. "Role of Electrode Design on the Volume of Tissue Activated During Deep Brain Stimulation," Journal of Neural Engineering, Mar. 1, 2006, vol. 3, No. 1, pp. 1-8.
Volkmann et al., Indroduction to the Programming of Deep Brain Stimulators, Movement Disorders, vol. 17, Suppl. 3, pp. S181-S187 (2002).
Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Schmidt et al. "Sketching and Composing Widgets for 3D Manipulation," Eurographics, Apr. 2008, vol. 27, No. 2, pp. 301-310.
Volkmann, J. , et al., "Basic algorithms for the programming of deep brain stimulation in Parkinson's disease", Mov Disord., 21 Suppl 14. (Jun. 2006),S284-9.
Walter, B. L., et al., "Surgical treatment for Parkinson's disease", Lancet Neural. 3(12). (Dec. 2004),719-28.

Wei, X. F., et al., "Current density distributions, field distributions and impedance analysis of segmented deep brain stimulation electrodes", J Neural Eng .. 2(4). (Dec. 2005), 139-47.
Zonenshayn, M. , et al., "Location of the active contact within the subthalamic nucleus (STN) in the treatment of idiopathic Parkinson's disease.", Surg Neurol., 62(3) (Sep. 2004),216-25.
Da Silva et al (A primer on diffusion tensor imaging of anatomical substructures. Neurosurg Focus 15(1): p. 1-4, Article 4, 2003.).
Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.
Grill, W. M., "Stimulus waveforms for selective neural stimulation", IEEE Engineering in Medicine and Biology Magazine, 14(4}, (Jul.-Aug. 1995), 375-385.
Miocinovic, S., et al., "Sensitivity of temporal excitation properties to the neuronal element activated by extracellular stimulation", J Neurosci Methods. 132(1). (Jan. 15, 2004), 91-9.
Hunka, K. et al., Nursing Time to Program and Assess Deep Brain Stimulators in Movement Disorder Patients, J. Neursci Nurs., 37: 204-10 (Aug. 2005).
Moss, J. , et al., "Electron microscopy of tissue adherent to explanted electrodes in dystonia and Parkinson's disease", Brain, 127{Pt 12). (Dec. 2004),2755-63.
Montgomery, E. B., et al., "Mechanisms of deep brain stimulation and future technical developments.", Neurol Res. 22(3). (Apr. 2000),259-66.
Merrill, D. R., et al., "Electrical stimulation of excitable tissue: design of efficacious and safe protocols", J Neurosci Methods. 141(2), (Feb. 15, 2005), 171-98.
Fisekovic et al., "New Controller for Functional Electrical Stimulation Systems", Med. Eng. Phys. 2001; 23:391-399.
Zhang, Y., et al., "Atlas-guided tract reconstruction for automated and comprehensive examination of the white matter anatomy," Neuroimage 52(4) (2010), pp. 1289-1301.
""BioPSE" The Biomedical Problem Solving Environment", htt12://www.sci.utah.edu/cibc/software/index.html, MCRR Center for integrative Biomedical Computing,(2004).
Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003),1-13.
Carnevale, N.T. et al., "The Neuron Book," Cambridge, UK: Cambridge University Press (2006), 480 pages.
Chaturvedi: "Development of Accurate Computational Models for Patient-Specific Deep Brain Stimulation," Electronic Thesis or Dissertation, Jan. 2012, 162 pages.
Chaturvedi, A. et al.: "Patient-specific models of deep brain stimulation: Influence of field model complexity on neural activation predictions." Brain Stimulation, Elsevier, Amsterdam, NL, vol. 3, No. Apr. 2, 2010, pp. 65-77.
Frankemolle, et al., "Reversing cognitive-motor impairments in Parkinson's disease patients using a computational modeling approach to deep brain stimulation programming," Brian 133 (2010), pp. 746-761.
McIntyre, C.C., et al., "Modeling the excitablitity of mammalian nerve fibers: influence of afterpotentials on the recovery cycle," J Neurophysioi, 87(2) (Feb. 2002), pp. 995-1006.
Peterson, et al., "Predicting myelinated axon activation using spatial characteristics of the extracellular field," Journal of Neural Engineering, 8 (2011), 12 pages.
Warman, et al., "Modeling the Effects of Electric Fields on nerver Fibers; Dermination of Excitation Thresholds,"IEEE Transactions on Biomedical Engineering, vol. 39, No. 12 (Dec. 1992), pp. 1244-1254.
Wesselink, et al., "Analysis of Current Density and Related Parameters in Spinal Cord Stimulation," IEEE Transactions on Rehabilitation Engineering, vol. 6, No. Jun. 2, 1998, pp. 200-207.
Andrews, R. J., "Neuroprotection trek—the next generation: neuromodulation II. Applications—epilepsy, nerve regeneration, neurotrophins.", Ann NY Acad Sci. 993 (May 2003), 14-24.

(56) References Cited

OTHER PUBLICATIONS

Astrom, M., et al., "The effect of cystic cavities on deep brain stimulation in the basal ganglia: a simulation-based study", J Neural Eng., 3(2), (Jun. 2006).132-8.
Bazin et al., "Free Software Tools for Atlas-based Volumetric Neuroimage Analysis", Proc. SPIE 5747, Medical Imaging 2005: Image Processing, 1824 May 5, 2005.
Back, C., et al., "Postoperative Monitoring of the Electrical Properties of Tissue and Electrodes in Deep Brain Stimulation", Neuromodulation, 6(4), (Oct. 2003 ),248-253.
Baker, K. B., et al., "Evaluation of specific absorption rate as a dosimeter of MRI-related implant heating", J Magn Reson Imaging., 20(2), (Aug. 2004),315-20.
Brown, J."Motor Cortex Stimulation," Neurosurgical Focus ( Sep. 15, 2001) 11 (3):E5.
Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and anti-opioid peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576 (2002).
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.
Bedard, C., et al., "Modeling extracellular field potentials and the frequency-filtering properties of extracellular space", Biophys J .. 86(3). (Mar. 2004),1829-42.
Benabid, A. L., et al., "Future prospects of brain stimulation", Neurol Res.;22(3), (Apr. 2000),237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.
Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.
Mcintyre, Cameron C., et al., "Cellular effects of deep brain stimulation: model-based analysis of activation and inhibition," J Neurophysioi, 91(4) (Apr. 2004), pp. 1457-1469.
Chaturvedi, A., et al.,, "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science; LNCS, Springer, Berlin, DE.
Butson, C. R., et al., "Deep brainstimulation interactive visualization system", Society for Neuroscience vol. 898.7 (2005).
Hodaie, M., et ai., "Chronic anterior thalamus stimulation for intractable epilepsy," Epilepsia, 43(6) (Jun. 2002), pp. 603-608.
Hoekema, R., et al., "Multigrid solution of the potential field in modeling electrical nerve stimulation," Comput Biomed Res., 31(5) (Oct. 1998), pp. 348-362.
Holsheimer, J., et al., "Identification of the target neuronal elements in electrical deep brain stimulation," Eur J Neurosci., 12(12) (Dec. 2000), pp. 4573-4577.
Jezernik, S., et al., "Neural network classification of nerve activity recorded in a mixed nerve," Neurol Res., 23(5) (Jul. 2001), pp. 429-434.
Jones, DK., et al., "Optimal strategies for measuring diffusion in anisotropic systems by magnetic resonance imaging," Magn. Reson. Med., 42(3) (Sep. 1999), pp. 515-525.

Krack, P., et al., "Postoperative management of subthalamic nucleus stimulation for Parkinson's disease," Mov, Disord., vol. 17(suppl 3) (2002), pp. 188-197.
Le Bihan, D., et al., "Diffusion tensor imaging: concepts and applications," J Magn Reson Imaging, 13(4) (Apr. 2001), pp. 534-546.
Lee, D. C., et al., "Extracellular electrical stimulation of central neurons: quantitative studies," In: Handbook of neuroprosthetic methods, WE Finn and PG Lopresti (eds) CRC Press (2003), pp. 95-125.
Levy, AL., et al., "An Internet-connected, patient-specific, deformable brain atlas integrated into a surgical navigation system," J Digit Imaging, 10(3 Suppl 1) (Aug. 1997), pp. 231-237.
Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.
Mcintyre, C. C., et al., "Extracellular stimulation of central neurons: influence of stimulus waveform and frequency on neuronal output," J. Neurophysiol., 88(4), (Oct. 2002), pp. 1592-1604.
Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.
Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.
Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.
Mcintyre, C. C., et al.,, Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.
Mcintyre, Cameron C., et al., "Modeling the excitability of mammalian nerve fibers: influence of aflerpotentials on the recovery cycle," J Neurophysioi, 87(2) (Feb. 2002), pp. 995-1006.
Mcintyre, Cameron C., et al., "Selective microstimulation of central nervous system neurons," Annals of biomedical engineering, 28(3) (Mar. 2000), pp. 219-233.
Mcintyre, C. C., et al., "Sensitivity analysis of a model of mammalian neural membrane," Biol Cybern., 79(1) (Jul. 1998), pp. 29-37.
Mcintyre, Cameron C., et al., "Uncovering the mechanism(s) of action of deep brain stimulation: activation, inhibition, or both," Clin Neurophysioi, 115(6) (Jun. 2004), pp. 1239-1248.
Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.
Mouine et al. "Multi-Strategy and Multi-Algorithm Cochlear Prostheses", Biomed. Sci. Instrument, 2000; 36:233-238.
Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.
Mcintyre, Cameron C., et al., "Electric field generated by deep brain stimulation of the subthalamic nucleus," Biomedical Engineering Society Annual Meeting, Nashville TN (Oct. 2003), 16 pages.
Mcintyre, Cameron C., et al., "Excitation of central nervous system neurons by nonuniform electric fields," Biophys. J., 76(2) (1999), pp. 878-888.
McNeal, DR., et al., "Analysis of a model for excitation of myelinated nerve," IEEE Trans Biomed Eng., vol. 23 (1976). pp. 329-337.
Micheli-Tzanakou, E., et al., "Computational Intelligence for target assesment in Parkinson's disease," Proceedings of SPIE vol. 4479,

(56) References Cited

OTHER PUBLICATIONS

Applications and Science of Neural Networks, Fuzzy Systems, and Evolutionary Computation IV (2001), pp. 54-69.

Miocinovic, S., et al., "Computational analysis of subthalamic nucleus and lenticular fasciculus activation during therapeutic deep brain stimulation," J Neurophysiol., 96(3) (Sep. 2006), pp. 1569-1580.

Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001), p. 1540.

Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Enginering, 50(9) (Sep. 2003), pp. 1074-1085.

Moffitt, MA., et al., "Prediction of myelinated nerve fiber stimulation thresholds: limitations of linear models," IEEE Transactions on Biomedical Engineering, 51 (2) (2003), pp. 229-236.

Moro, E, et al., "The impact on Parkinson's disease of electrical parameter settings in STN stimulation," Neurology, 59 (5) (Sep. 10, 2002). pp. 706-713.

Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.

Nowak, LG., et al., "'Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.

O'Suilleabhain, PE., et al., "Tremor response to polarity, voltage, pulsewidth and frequency of thalamic stimulation," Neurology, 60(5) (Mar. 11, 2003), pp. 786-790.

Pierpaoli, C., et al., "Toward a quantitative assessment of diffusion anisotropy," Magn Reson Med., 36(6) (Dec. 1996), pp. 893-906.

Plonsey, R., et al., "Considerations of quasi-stationarity in electrophysiological systems," Bull Math Biophys., 29(4) (Dec. 1967), pp. 657-664.

Ranck, J B., "Specific impedance of rabbit cerebral cortex," Exp. Neurol., vol. 7 (Feb. 1963), pp, 144-152.

Ranck, J B., et al., "The Specific impedance of the dorsal columns of the cat: an anisotropic medium," Exp. Neurol., 11 (Apr. 1965), pp. 451-463.

Ranck, J B., "Which elements are excited in electrical stimulation of mammalian central nervous system: a review," Brain Res., 98(3) (Nov. 21, 1975), pp. 417-440.

Rattay, F., et al., "A model of the electrically excited human cochlear neuron. I. Contribution of neural substructures to the generation and propagation of spikes," Hear Res., 153(1-2) (Mar. 2001), pp. 43-63.

Rattay, F., "A model of the electrically excited human cochlear neuron. II. Influence of the three-dimensional cochlear structure on neural excitability," Hear Res., 153(1-2) (Mar. 2001), pp. 64-79.

Rattay, F., "Arrival at Functional Electrostimulation by modelling of fiber excitation," Proceedings of the Ninth annual Conference of the IEEE Engineering in Medicine and Biology Society (1987), pp. 1459-1460.

Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.

Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.

Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.

Sances, A., et al., "In Electroanesthesia: Biomedical and Biophysical Studies," A Sances and SJ Larson, Eds., Academic Press, NY (1975), pp. 114-124.

SI. Jean, P., et al., "Automated atlas integration and interactive three-dimensional visualization tools for planning and guidance in functional neurosurgery," IEEE Transactions on Medical Imaging, 17(5) (1998), pp. 672-680.

Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.

Sterio, D., et al., "Neurophysiological refinement of subthalamic nucleus targeting," Neurosurgery, 50(1) (Jan. 2002), pp. 58-69.

Struijk, J. J., et al., "Excitation of dorsal root fibers in spinal cord stimulation: a theoretical study," IEEE Transactions on Biomedical Engineering, 40(7) (Jul. 1993), pp. 632-639.

Struijk, J J., et al., "Recruitment of dorsal column fibers in spinal cord stimulation: influence of collateral branching," IEEE Transactions on Biomedical Engineering, 39(9) (Sep. 1992), pp. 903-912.

Tamma, F., et al., "Anatomo-clinical correlation of intraoperative stimulation-induced side-effects during HF-DBS of the subthalamic nucleus," Neurol Sci., vol. 23 (Suppl 2) (2002), pp. 109-110.

Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.

Testerman, Roy L., "Coritical response to callosal stimulation: a model for determining safe and efficient stimulus parameters," Annals of Biomedical Engineering, 6(4) (1978), pp. 438-452.

Tuch, D.S., et al., "Conductivity mapping of biological tissue using diffusion MRI," Ann NY Acad Sci., 888 (Oct. 30, 1999), pp. 314-316.

Tuch, D.S., et al., "Conductivity tensor mapping of the human brain using diffusion tensor MRI," Proc Nall Acad Sci USA, 98(20) (Sep. 25, 2001), pp. 11697-11701.

Veraart, C., et al., "Selective control of muscle activation with a multipolar nerve cuff electrode," IEEE Transactions on Biomedical Engineering, 40(7) (Jul. 1993), pp. 640-653.

Vercueil, L., et al., "Deep brain stimulation in the treatment of severe dystonia," J. Neural., 248(8) (Aug. 2001), pp. 695-700.

Vilalte, "Circuit Design of the Power-on-Reset," Apr. 2000, pp. 1-25.

Vitek, J. L., "Mechanisms of deep brain stimulation: excitation or inhibition," Mov. Disord., vol. 17 (Suppl. 3) (2002), pp. 69-72.

Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.

Wakana, S., et al., "Fiber tract-based atlas of human white matter anatomy," Radiology, 230(1) (Jan. 2004), pp. 77-87.

Alexander, DC., et al., "Spatial transformations of diffusion tensor magnetic resonance images," IEEE Transactions on Medical Imaging, 20 (11), (2001), pp. 1131-1139.

Wu, Y. R., et al., "Does Stimulation of the GPi control dyskinesia by activating inhibitory axons?," Mov. Disord., vol. 16 (2001), pp. 208-216.

Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.

Yianni, John, et al., "Globus pallidus internus deep brain stimulation for dystonic conditions: a prospective audit," Mov. Disord., vol. 18 (2003), pp. 436-442.

Zonenshayn, M., et al., "Comparison of anatomic and neurophysiological methods for subthalamic nucleus targeting," Neurosurgery, 47(2) (Aug. 2000), pp. 282-294.

Voghell et al., "Programmable Current Source Dedicated to Implantable Microstimulators" ICM '98 Proceedings of the Tenth International Conference, pp. 67-70, 1993.

Butson, Christopher R., et al., "Patient-specific analysis of the volume of tissue activated during deep brain stimulation", NeuroImage. vol. 34. (2007),661-670.

(56) References Cited

OTHER PUBLICATIONS

Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.
Alo, K. M., et al., "New trends in neuromodulation for the management of neuropathic pain," Neurosurgery, 50(4), (Apr. 2002), pp. 690-703, discussion pp. 703-704.
Ashby, P., et al., "Neurophysiological effects of stimulation through electrodes in the human subthalamic nucleus," Brain, 122 (PI 10), (Oct. 1999), pp. 1919-1931.
Baker, K. B., et al., "Subthalamic nucleus deep brain stimulus evoked potentials: Physiological and therapeutic implications," Movement Disorders, 17(5), (Sep./Ocl. 2002), pp. 969-983.
Bammer, R, et al., "Diffusion tensor imaging using single-shot SENSE-EPI", Magn Reson Med., 48(1 ), (Jul. 2002). pp. 128-136.
Basser, P J., et al,, "MR diffusion tensor spectroscopy and imaging," Biophys J., 66(1 ), (Jan. 1994), pp. 259-267.
Basser, P J., et al., "New currents in electrical stimulation of excitable tissues," Annu Rev Biomed Eng., 2, (2000), pp. 377-397.
Benabid, AL., et al., "Chronic electrical stimulation of the ventralis intermedius nucleus of the thalamus as a treatment of movement disorders," J. Neurosurg., 84(2), (Feb. 1996), pp. 203-214.
Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.
Benabid, A L., et al., "Long-term suppression of tremor by chronic stimulation of the ventral intermediate thalamic nucleus," Lancet, 337 (8738), (Feb. 16, 1991 ), pp. 403-406.
Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.
Christensen, Gary E., et al., "Volumetric transformation of brain anatomy," IEEE Transactions on Medical Imaging, 16 (6), (Dec. 1997), pp. 864-877.
Cooper, S , et al, "Differential effects of thalamic stimulation parameters on tremor and paresthesias in essential tremor," Movement Disorders, 17(Supp. 5), (2002), p. S193.
Coubes, P, et al., "Treatment of DYT1-generalised dystonia by stimulation of the internal globus pallidus," Lancet, 355 (9222), (Jun. 24, 2000), pp. 2220-2221.
Dasilva, A.F. M., et al., "A Primer Diffusion Tensor Imaging of Anatomical Substructures," Neurosurg. Focus; 15(1) (Jul. 2003), pp. 1-4. _____ ---;.
Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.
Finnis, K. W., et al., "3-D functional atalas of subcortical structures for image guided stereotactic neurosurgery," Neuroimage, vol. 9, No. 6, lss. 2 (1999), p. S206.
Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.
Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes in Computer Science; vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11, Lecture Notes in Computer Science; vol. 2489 (2002), pp. 69-76.
Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.
Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al, "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.
Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol., 48(3) (Sep. 2000), pp. 372-376.

(56) References Cited

OTHER PUBLICATIONS

Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.

Hanekom, "Modelling encapsulation tissue around cochlear implant electrodes," Med. Biol. Eng. Comput. vol. 43 (2005), pp. 47-55.

Haueisen, J , et al., "The influence of brain tissue anisotropy on human EEG and MEG," Neuroimage, 15(1) (Jan. 2002), pp. 159-166.

D'Haese et al. Medical Image Computing and Computer-Assisted Intervention—MICCAI 2005 Lecture Notes in Computer Science, 2005, vol. 3750, 2005, 427-434.

Rohde et al. IEEE Transactions on Medical Imaging, vol. 22 No. 11, 2003 p. 1470-1479.

Dawant et al., Biomedical Image Registration. Lecture Notes in Computer Science, 2003, vol. 2717, 2003, 142-150.

Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.

Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.

Acar et al., "Safety Anterior Commissure-Posterior Commissure-Based Target Calculation of the Subthalamic Nucleus in Functional Stereotactic Procedures", Stereotactic Funct, Neurosure., 85:287-291, Aug. 2007.

Andrade-Souza, "Comparison of Three Methods of Targeting the Subthaiamic Nucleus for Chronic Stimuiation in Parkinson's Disease", Neurosurgery, 56:360-368, Apr. 2005.

Anheim et al., "Improvement in Parkinson Disease by Subthalamic Nucleus Stimulation Based on Electrode Placement", Arch Neural., 65:612-616, May 2008

Butson et al., "Tissue and Electrode Capacitance Reduce Neural Activation Volumes During Deep Brain Stimulation", Clinical Neurophysiology, 116:2490-2500, Oct. 2005.

Butson et al., "Sources and Effects of Electrode Impedance During Deep Brain Stimulation", Clinical Neurophysiology, 117:44 7-454, Dec. 2005.

D'Haese et al., "Computer-Aided Placement of Deep Brain Stimulators: From Planning to Intraoperative Guidance", IEEE Transaction on Medical Imaging, 24:1469-1478, Nov. 2005.

Gross et al., "Electrophysiological Mapping for the Implantation of Deep Brain Stimulators for Parkinson's Disease and Tremor", Movement Disorders, 21 :S259-S283, Jun. 2006.

Halpern et al., "Brain Shift During Deep Brain Stimulation Surgery for Parkinson's Disease". Stereotact Funct. Neurosurg., 86:37-43, published online Sep. 2007.

Herzog et al., "Most Effective Stimulation Site in Subthalamic Deep Brain Stimulation for Parkinson's Disease", Movement Disorders, 19:1050-1099, published on line Mar. 2004.

Jean et al., A Feasibility Study of Optical Coherence Tomography for Guiding Deep Brain Probes, Journal of Neuroscience Methods, 154:96-101, Jun. 2006.

Khan et al., "Assessment of Brain Shift Related to Deep Brain Stimulation Surgery", Sterreotact Funct. Neurosurg., 86:44-53, published online Sep. 2007.

Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.

Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.

Machado et al., "Deep Brain Stimulation for Parkinson's Disease: Surgical Technique and Perioperative Management", Movement Disorders, 21 :S247-3258, Jun. 2006.

Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.

Moran et al., "Real-Time Refinment of Subthalamic Nucleous Targeting Using Bayesian Decision-Making on the Root Mean Square Measure", Movement Disorders, 21: 1425-1431, published online Jun. 2006.

Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.

Winkler et al., The First Evaluation of Brain Shift During Functional Neurosurgery by Deformation Field Analysis, J. Neural. Neurosurg, Psychiatry, 76:1161-1163, Aug. 2005.

Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.

Ward, H. E., et al., "Update on deep brain stimulation for neuropsychiatric disorders," Neurobiol Dis 38 (3) (2010), pp. 346-353.

Alberts et al. "Bilateral subthalamic stimulation impairs cognitive-motor performance in Parkinson's disease patients." Brain (2008), 131, 3348-3360, Abstract.

Butson, Christopher R., et al., "Sources and effects of electrode impedance during deep brain stimulation", Clinical Neurophysiology. vol. 117.(2006),447-454.

An, et al., "Prefronlal cortical projections to longitudinal columns in the midbrain periaqueductal gray in macaque monkeys," J Comp Neural 401 (4) (1998), pp. 455-479.

Bulson, C. R., et al., "Tissue and electrode capacitance reduce neural activation volumes during deep brain stimulation," Clinical Neurophysiology, vol. 116 (2005), pp. 2490-2500.

Carmichael, S. T., et al., "Connectional networks within the orbital and medial prefronlal cortex of macaque monkeys," J Comp Neural 371 (2) (1996), pp. 179-207.

Croxson, et al., "Quantitative investigation of connections of the prefronlal cortex in the human and macaque using probabilistic diffusion tractography," J Neurosci 25 (39) (2005), pp. 8854-8866.

Frankemolle, et al., "Reversing cognitive-motor impairments in Parkinson's disease patients using a computational modelling approach to deep brain stimulation programming," Brain 133 (2010). pp. 746-761.

Freedman, et al., "Subcortical projections of area 25 (subgenual cortex) of the macaque monkey," J Comp Neurol 421 (2) (2000), pp. 172-188.

Giacobbe, et al., "Treatment resistant depression as a failure of brain homeostatic mechanisms: implications for deep brain stimulation," Exp Neural 219 (1) (2009), pp. 44-52.

Goodman, et al., "Deep brain stimulation for intractable obsessive compulsive disorder: pilot study using a blinded, staggered-onset design," Biol Psychiatry 67 (6) (2010), pp. 535-542.

Greenberg, et al., "Deep brain stimulation of the ventral internal capsule/ventral striatum for obsessive-compulsive disorder: worldwide experience," Mol Psychiatry 15 (1) (2010), pp. 64-79.

Greenberg. et al., "Three-year outcomes in deep brain stimulation for highly resistant obsessive-compulsive disorder," Neuropsychopharmacology 31 (11) (2006), pp. 2384-2393.

Gutman, et al., "A tractography analysis of two deep brain stimulation white matter targets for depression," Biol Psychiatry 65 (4) (2009), pp. 276-282.

Haber, et al., "Reward-related cortical inputs define a large striatal region in primates that interface with associative cortical connections, providing a substrate for incentive-based learning," J Neurosci 26 (32) (2006), pp. 8368-8376.

Haber, et al., "Cognitive and limbic circuits that are affected by deep brain stimulation," Front Biosci 14 (2009), pp. 1823-1834

Hines, M. L., et al., "The NEURON simulation environment," Neural Comput., 9(6) (Aug. 15, 1997), pp. 1179-1209.

Hua, et al., "Tract probability maps in stereotaxic spaces: analyses of white matter anatomy and tract-specific quantification," Neuroimage 39 (1) (2008), pp, 336-347.

(56) References Cited

OTHER PUBLICATIONS

Johansen-Berg, et al., "Anatomical connectivity of the subgenual cingulate region targeted with deep brain stimulation for treatment-resistant depression," Cereb Cortex 18 (6) (2008), pp. 1374-1383.
Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry 64 (6) (2008), pp. 461-467.
Lujan, et al., "Tracking the mechanisms of deep brain stimulation for neuropsychiatric disorders," Front Biosci 13 (2008), pp. 5892-5904.
Lujan, J.L. et al,. "Automated 3-Dimensional Brain Atlas Fitting to Microelectrode Recordings from Deep Brain Stimulation Surgeries," Stereotact. Funel. Neurosurg. 87(2009), pp. 229-240.
Machado. et al., "Functional topography of the ventral striatum and anterior limb of the internal capsule determined by electrical stimulation of awake patients," Ciin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Mayberg, H. S., et al., "Deep brain stimulation for treatment-resistant depression," Neuron, 45(5) (Mar. 3, 2005), pp. 650-660.
Mayberg, H. S., et al., "Limbic-cortical dysregulation: a proposed model of depression," J Neuropsychiatry Ciin Neurosci. 9 (3) (1997); pp. 471-481.
McIntyre,C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216 (i) (2009), pp. 166-176.
Nuttin, et al., "Electrical stimulation in anterior limbs of internal capsules in patients with obsessive-compulsive disorder," Lancet 354 (9189) (1999), p. 1526.
Saxena, et al., "Cerebral glucose metabolism in obsessive-compulsive hoarding," Am J Psychiatry. 161 (6) (2004), pp. 1038-1048.
Viola, et al., "Importance-driven focus of attention," IEEE Trans Vis Comput Graph 12 (5) (2006), pp. 933-940.
Wakana, S., et al., "Reproducibility of quantitative tractography methods applied to cerebral white matter," Neuroimage 36 (3) (2007), pp. 630-644.
Mayr et al., "Basic Design and Construction of the Vienna FES Implants: Existing Solutions and Prospects for New Generations of Implants", Medical Engineering & Physics, 2001; 23:53-60.
McIntyre, Cameron , et al, "Finite element analysis of the current-density and electric field generated by metal microelectrodes", Ann Biomed Eng . 29(3), (2001 ),227-235.
Foster, K. R., et al., "Dielectric properties of tissues and biological materials: a critical review.", Grit Rev Biomed Ena. 17(1 ). (1989),25-104.
Limousin, P., et al., "Electrical stimulation of the subthalamic nucleus in advanced Parkinson's disease", N Engl J Med .. 339(16), (Oct. 15, 1998), 1105-11.

Kitagawa, M., et al., "Two-year follow-up of chronic stimulation of the posterior subthalamic white matter for tremor-dominant Parkinson's disease.", Neurosurgery. 56(2). (Feb., 2005),281-9.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.
Holsheimer, J. , et al., "Chronaxie calculated from current-duration and voltage-duration data", J Neurosci Methods. 97(1). (Apr, 1, 2000),45-50.
Hines, M. L., et al., "The NEURON simulation environment", Neural Comput. 9(6). (Aug. 15, 1997), 1179-209.
Herzog, J., et al., "Most effective stimulation site in subthalamic deep brain stimulation for Parkinson's disease", Mov Disord. 19(9). (Sep. 2004),1050-4.
Hershey, T., et al., "Cortical and subcortical blood flow effects of subthalamic nucleus stimulation in PD.", Neurology 61(6). (Sep. 23, 2003),816-21.
Hemm, S. , et al., "Evolution of Brain Impedance in Dystonic Patients Treated by GPi Electrical Stimulation", Neuromodulation 7(2) (Apr. 2004),67-75.
Hemm, S., et al., "Deep brain stimulation in movement disorders: stereotactic coregistration of two-dimensional electrical field modeling and magnetic resonance imaging.", J Neurosurg. 103(6): (Dec. 2005),949-55.
Haueisen, J, et al., "The influence of brain tissue anisotropy on human EEG and MEG", Neuroimage 15(1) (Jan. 2002),159-166.
Haslinger, B., et al., "Frequency-correlated decreases of motor cortex activity associated with subthalamic nucleus stimulation in Parkinson's disease.", Neuroimage 28(3). (Nov. 15, 2005),598-606.
Hashimoto, T. , et al., "Stimulation of the subthalamic nucleus changes the firing pattern of pallidal neurons", J Neurosci, 23(5). (Mar. 1, 2003),1916-23.
Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.
Haiying, L., et al., "Intra-operative MR-guided DBS implantation for treating PD and ET", Proceedings of SPIE vol. 4319, Department of Radiology & Neurosurgery, University of Minnesota, Minneapolis, MN 55455,(2001 ),272-276.
Grill, WM., et al., "Electrical properties of implant encapsulation tissue", Ann Biomed Eng. vol. 22. (1994),23-33.
Grill, W. M., et al., "Deep brain stimulation creates an informational lesion of the stimulated nucleus", Neuroreport. 15I7t (May 19, 2004 ), 1137-40.
McNaughtan et al., "Electrochemical Issues in Impedance Tomography", 1st World Congress on Industrial Process Tomography, Buxton, Greater Manchester, Apr. 14-17, 1999.
Chaturvedi A et al: "Patient-specific models of deep brain stimulation: Influence of field model complexity on neural activation predictions," Brain Stimulation, Elsevier, Amsterdam, NL, vol. 3, No. 2, Apr. 1, 2010 (Apr. 1, 2010), pp. 65-77.
International Search Report and Written Opinion for PCT/US2015/042873 dated Jan. 19, 2016.
Kringelbach ML., Jenkinson N, Owen SL, Aziz TZ. Translational principles of deep brain stimulation. Nature Reviews Neuroscience. Aug. 2007;8(8):623.
Official Communication for U.S. Appl. No. 14/813,818 dated Sep. 28, 2018.
Official Communication for U.S. Appl. No. 14/813,818 dated Apr. 30, 2018.

SYSTEMS AND METHODS FOR STIMULATION-RELATED VOLUME ANALYSIS OF THERAPEUTIC EFFECTS AND OTHER CLINICAL INDICATIONS

CROSS-REFERENCE TO RELATED APPLICATIONS

This application is a continuation of U.S. patent application Ser. No. 14/813,818, filed Jul. 30, 2015, which claims the benefit under 35 U.S.C. § 119(e) of U.S. Provisional Patent Application Ser. No. 62/031,075, both of which are hereby incorporated herein by reference in their entirety.

FIELD OF THE INVENTION

Aspects of the present invention pertain to management of data in a central location for access at multiple locations, by various machines, and via various applications. Aspects of the present invention pertain to an interface of a stimulation setting remote control in a clinical mode. Aspects of the present invention pertain to sharing of target volumes of activation.

BACKGROUND

Electrical stimulation of an anatomical region, e.g., deep brain stimulation (DBS), such as of the thalamus or basal ganglia, is a clinical technique for the treatment of disorders such as essential tremor, Parkinson's disease (PD), and other physiological disorders. DBS may also be useful for traumatic brain injury and stroke. Pilot studies have also begun to examine the utility of DBS for treating dystonia, epilepsy, and obsessive-compulsive disorder.

A stimulation procedure, such as DBS, typically involves first obtaining preoperative images, e.g., of the patient's brain, such as by using a computed tomography (CT) scanner device, a magnetic resonance imaging (MRI) device, or any other imaging modality. This sometimes involves first affixing to the patient's skull spherical or other fiducial markers that are visible on the images produced by the imaging modality. The fiducial markers help register the preoperative images to the actual physical position of the patient in the operating room during the later surgical procedure.

After the preoperative images are acquired by the imaging modality, they are then loaded onto an image-guided surgical (IGS) workstation, and, using the preoperative images displayed on the IGS workstation, a neurosurgeon can select a target region, e.g., within the brain, an entry point, e.g., on the patient's skull, and a desired trajectory between the entry point and the target region. The entry point and trajectory are typically carefully selected to avoid intersecting or otherwise damaging certain nearby critical structures or vasculature, e.g., of the brain.

In the operating room, the physician marks the entry point on the patient's skull, drills a burr hole at that location, and affixes a trajectory guide device about the burr hole. The trajectory guide device includes a bore that can be aimed to obtain the desired trajectory to the target region. After aiming, the trajectory guide is locked to preserve the aimed trajectory toward the target region. After the aimed trajectory has been locked in using the trajectory guide, a microdrive introducer is used to insert the surgical instrument along the trajectory toward the target region, e.g., of the brain. The surgical instrument may include, among other things, a recording electrode leadwire, for recording intrinsic electrical signals, e.g., of the brain; a stimulation electrode leadwire, for providing electrical energy to the target region, e.g., of the brain; or associated auxiliary guidewires or guide catheters for steering a primary instrument toward the target region, e.g., of the brain.

The stimulation electrode leadwire, which typically includes multiple closely-spaced electrically independent stimulation electrode contacts, is then introduced to deliver the therapeutic stimulation to the target region, e.g., of the brain. The stimulation electrode leadwire is then immobilized, such as by using an instrument immobilization device located at the burr hole entry, e.g., in the patient's skull, in order for the DBS therapy to be subsequently performed.

The subthalamic nucleus (STN) represents the most common target for DBS technology. Clinically effective STN DBS for PD has typically used electrode contacts in the anterior-dorsal STN. However, STN DBS exhibits a low threshold for certain undesirable side effects, such as tetanic muscle contraction, speech disturbance and ocular deviation. Highly anisotropic fiber tracks are located about the STN. Such nerve tracks exhibit high electrical conductivity in a particular direction. Activation of these tracks has been implicated in many of the DBS side effects. However, there exists a limited understanding of the neural response to DBS. The three-dimensional (3-D) tissue medium near the DBS electrode typically includes both inhomogeneous and anisotropic characteristics. Such complexity makes it difficult to predict the particular volume of tissue influenced by DBS.

After the immobilization of the stimulation electrode leadwire, the actual stimulation therapy is often not initiated until after a time period of about two-weeks to one month has elapsed. This is due primarily to the acute reaction of the brain tissue to the introduced electrode leadwire (e.g., the formation of adjacent scar tissue), and stabilization of the patient's disease symptoms. At that time, a particular one or more of the stimulation electrode contacts is selected for delivering the therapeutic stimulation, and other stimulation parameters are adjusted to achieve an acceptable level of therapeutic benefit.

A system and method may estimate stimulation volumes, and display models of a patient anatomy and/or a stimulation leadwire, via which to graphically identify the estimated stimulation volumes and how they interact with various regions of the patient anatomy.

The systems and methods may be used to explore target regions of stimulation and stimulation therapies to determine which therapy regimen is best suited for a particular patient or group of patients.

SUMMARY

Such exploration may result in much data over time for a particular patient and/or for a patient population. Example embodiments of the present invention provide a system and methods to improve the quality of such data, to manage such data, and to maximize use of, and facilitate efficient use of, such information.

The data may pertain to, for example, stimulation of a patient for deep brain stimulation (DBS) therapy and/or spinal cord stimulation (SCS) therapy. It may include graphical information, such as estimated volumes of activation (VOA), also referred to herein as a stimulation field model (SFM). It may include information used for rendering the SFMs, such as image registration and/or leadwire location data. It may further include information regarding the patient's condition, such as disease and medications taken, and/or reactions to an applied therapy. It may further include information concerning stimulation programs applied to the patient for the patient therapy. It may include target volumes selected for a patient, and/or volumes of estimated activation (VOA) for various stimulation parameters input for the patient. It may include information concerning how close the patient's anatomical images match to a standard atlas. It may further include analytics information as described below.

Various systems, system components, and/or program modules may be used for performance of various tasks associated with, or that provide an output usable for, providing therapeutic stimulation, generation of data regarding a therapy, and access to and transfer of therapy data. Embodiments of the present invention provide for communication and/or between the various systems, system components, and/or program modules.

The various methods described herein may be practiced, each alone, or in various combinations.

An example embodiment of the present invention is directed to a processor, which may be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination. In certain example embodiments, the processor may be embodied in a remote control device. The memory device may include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to a hardware computer-readable medium, e.g., as described above, having stored thereon instructions executable by a processor to perform the methods described herein.

An example embodiment of the present invention is directed to a method, e.g., of a hardware component or machine, of transmitting instructions executable by a processor to perform the methods described herein.

DETAILED DESCRIPTION

Figure 1:
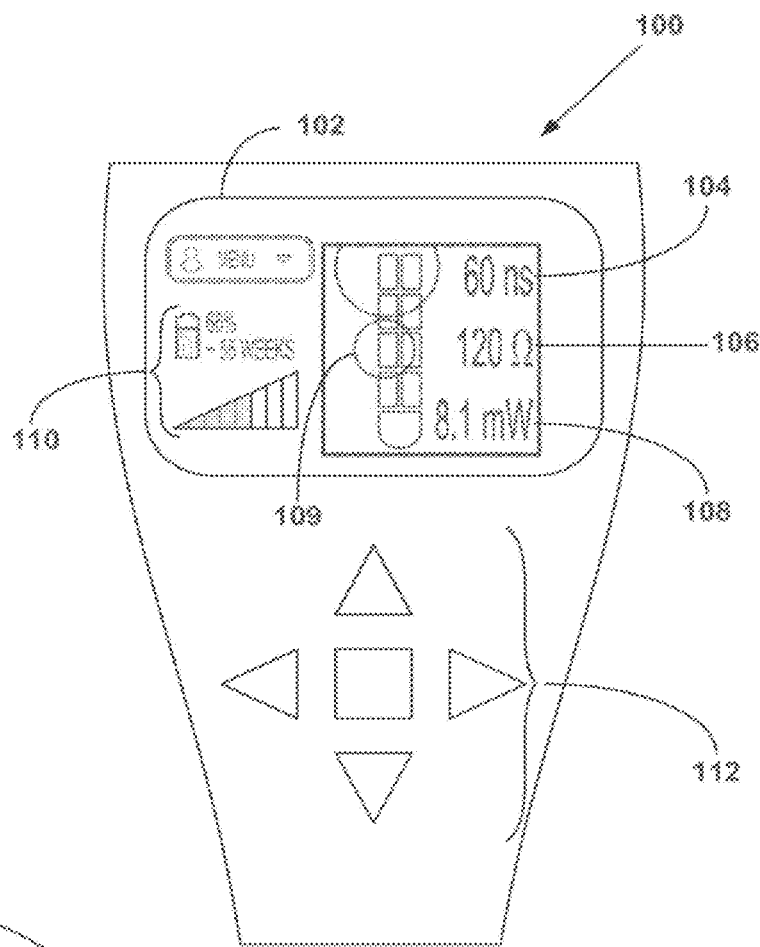
FIG. 1 illustrates a remote control device according to an example embodiment of the present invention.

Aspects of the present invention pertain to management of data in a central location for access at multiple locations, by various machines, and via various applications. Aspects of the present invention pertain to an interface of a stimulation setting remote control in a clinical mode. Aspects of the present invention pertain to sharing of target volumes of activation. The applications and systems via which the various data is created and/or accessed and/or used and/or in which the described interfaces may be presented may include any one of those described in U.S. patent application Ser. No. 12/454,330, filed May 15, 2009 ("the '330 application"), U.S. patent application Ser. No. 12/454,312, filed May 15, 2009 ("the '312 application"), U.S. patent application Ser. No. 12/454,340, filed May 15, 2009 ("the '340 application"), U.S. patent application Ser. No. 12/454,343, filed May 15, 2009 ("the '343 application"), U.S. patent application Ser. No. 12/454,314, filed May 15, 2009 ("the '314 application"), U.S. Provisional Pat. App. Ser. No. 61/468,884, filed Mar. 29, 2011 ("the '884 application"), U.S. Provisional Pat. App. Ser. No. 61/468,887, filed Mar. 29, 2011 ("the '887 application"), U.S. Provisional Pat. App. Ser. No. 61/468,891, filed Mar. 29, 2011 ("the '891 application"), U.S. Provisional Pat. App. Ser. No. 61/468,897, filed Mar. 29, 2011 ("the '897 application"), and U.S. Provisional Pat. App. Ser. No. 61/468,901, filed Mar. 29, 2011 ("the '901 application"), the content of each of which is hereby incorporated herein by reference in its entirety.

Aspects of the present application pertain to subject matter described in U.S. patent application Ser. Nos. 13/571,078 and 13/570,998, the content of both of which were filed Aug. 9, 2012 and are hereby incorporated by reference herein in their entireties. Aspects of the present invention also pertain to subject matter described in U.S. Provisional Patent Application Ser. Nos. 61/521,626 filed on Aug. 9, 2011, 61/521,641 filed on Aug. 9, 2011, 61/521,632 filed on Aug. 9, 2011, 61/676,000 filed on Jul. 26, 2012 and 61/676,014 filed on Jul. 26, 2012, the content of all of which are hereby incorporated by reference herein in their entireties.

Aspects of the present application also pertain to subject matter described in U.S. patent application Ser. No. 13/431,232 ("the '232 application) filed Mar. 27, 2012, which claims priority to U.S. Prov. Pat App. Ser. Nos. 61/468,884, 61/468,887, 61/468,891, 61/468,897, and 61/468,901 which were all filed Mar. 29, 2011. The contents of each of these applications are also incorporated by reference herein in their entireties.

Cloud Data Management

A Guide software for stimulation therapy may require various data used at various points of time. Example embodiments of the present invention provide for getting the information to go to the right place at the right time. Additionally, example embodiments allow for patient data to travel with the patient. Information may include the graphics, but may also include other non-imagery data, as noted above, such as side effects, tremors (e.g., measured by an accelerometer in the implantable pulse generator (IPG)), medications, and other clinical data that may be updated over time.

In an example embodiment of the present invention, a patient can be assigned and given an identification (ID) card that has the patient's data. For example, the card may be inserted into, or otherwise be provided in communication with, a computer and data on the computer may be recorded on the card. However, as explained in connection with the alternative embodiments below, the data need not be stored on the card, and the card would then only be used for obtaining access to the data, which can be stored remotely, for example, in a central server.

In an alternative example embodiment, the patient has a card that includes a pin number that one can use to access the patient's information.

In an alternative example embodiment, the patient has a card that includes an account number that, when input to a computer along with a pin number from the user's memory, allows access to the patient's information.

In an alternative example embodiment, the card includes a number that, when the card is swiped in a device connected to a computer, is read by the computer, and that thereby allows access to the data of the patient associated with the number. In an example embodiment, the number can be one on the patient's implanted IPG, which is already managed to have unique numbers. Use of such a number, rather than patient name, can help with anonymization issues. That is, the data is stored in connection with a number, rather than in association with data by which can identify the patient.

A problem is where data is recorded before the user obtains the IPG. In this instance, a temporary number may be assigned, and then, when the IPG is implanted, a switchover may be made to the number of the IPG.

Use of the IPG number may be advantageous because even if the user loses the card, the user can obtain the information by using the IPG which obviously does not get lost.

In an example embodiment of the present information the IPG may transmit a signal with the number. According to this embodiment, the card may be omitted. Instead, the signal of the IPG indicating the unique number (or any unique signal that may be omitted by the IPG which unique signal is associated with the particular patient) may allow the data access. Not only the IPG, but any RFID device provided to the user can be used to provide the number. However, it is preferred to use a device implanted in the patient, so that it is ensured not to be lost.

The computer may "talk" to the signaling device on the patient to get the number needed to obtain (or send to the server) the information. For example, the user may connect a device to a port of a computer (e.g., a USB port, a serial port or any other communications port), which device is configured to receive a signal from the IPG, which indicates some number. The number is sent to the central server and then the information is obtained. This can be beneficial for security purposes as well because it allows the system to be controlled not to send the information unless the device recognizes that the patient with the correct IPG is physically present at the computer terminal at which the information is being requested or via which information is being stored.

The guide system, including the visualization package, the clinician programmer (CP) by which the clinician actually programs the IPG, or the patient programmer system by which the IPG settings can be changed without the clinician, and the analytic system (described below) can each access the information in the cloud. In an example embodiment, any web browser may be used to access the information.

Different users can have different types of access. For example, a patient may have a certain level of access, a health care provider may have another level of access, and a relative (who is not the health care provider) can have yet another level of access.

In an example embodiment, the IPG may be programmed to generate, based on a user-input code, a second code that provides a specific level of access. The second code may be unique to the user (e.g., a particular health care provider). In this manner, different levels of access may be provided to data generated using the same IPG. Thus, for example, a health care provider may only be able to access IPG data generated at the provider's facility, but may not have access to IPG data generated at other provider facilities, even though the IPG is the same.

In an example embodiment, health care providers may be provided with the ability to access the data without the patient (and therefore the IPG) being physically present. For example, the provider may store the patient's access credentials (e.g., IPG number) the first time the patient visits, so that patient data can be obtained prior to the next visit.

Additional data that can be included in the central location for access as described above is analytics information as described below and the data used for the analytics.

Additional information stored in the cloud can be a log of the changes entered by the patients to their parameters using the remote control, which changes could be time-stamped, as described below. The remote control will record the information. The remote control can be plugged into a computer which then sends it to the central location for storage in association with the number that is unique to the patient. Alternatively, it can be sent continuously or periodically through, e.g., a wireless connection, e.g., via a cellular connection. Alternatively, the remote control can connect to a device through a wireless connection, and, when so connected, it can send the information to the central server.

Additionally, the detailed computations—fusion of MR/CT, fusion of atlas to MR, lead location, VOA generation, etc. (see all computations and data described in the '330, '312, '340, '343, '314, '884, '887, '891, '897, and '901 applications)—can be performed at a server and the resulting information can be stored centrally.

In an example embodiment, transformation matrix parameters can be stored centrally. For example, the central server, the IPG, and/or the remote used by the patient would store the transformation matrices, such as how to transform the atlas to the patient's MR. Additionally, it could store the location of the lead in the resulting patient-specific atlas. It could also store an atlas identifier to identify which atlas is the one being transformed, in case different atlases are used at different times, e.g., because of a software upgrade.

In an example embodiment of the present invention, information from sensors monitoring a patient condition, for example, while stimulation is being performed, immediately thereafter, or during a longer period spanning a stimulation therapy including periods of on and off stimulation states, is uploaded to a cloud data store which is accessible by clinicians, doctors, and/or the patient logging into various stimulation control modules, e.g., a stimulation programming and/or planning module. According to an example embodiment, the sensor information is associated with VOAs as further described below which is used for patient population analytics, as further described below.

Figure 13:
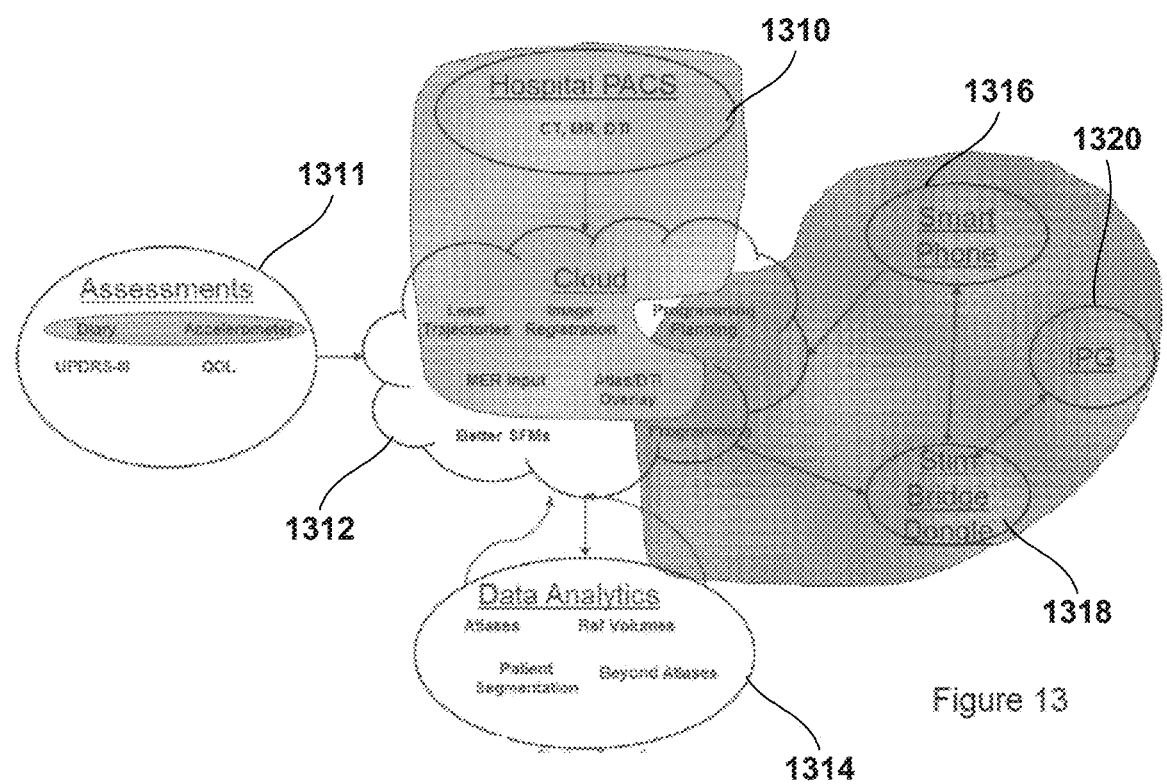
FIG. 13 illustrates a cloud management paradigm with integration of a hospital image system, e.g., picture archiving and communication system (PACS), patient record system including information on patient assessments, a patient programming system, and a patient analytics system, according to an example embodiment of the present invention.

FIG. 13 illustrates a cloud management paradigm with integration of a hospital image system, e.g., picture archiving and communication system (PACS) 1310, patient record system including information on patient assessments 1311, a patient programming system, and a patient analytics system. Patient records, including assessments are uploadable to a central cloud data store 1312. Patient images are also uploadable from the PACS system to the cloud data store. Data analytics 1314 as described below are also uploadable to the cloud 1312. The cloud may include a server which maintains programs accessible from terminals, e.g., over the Internet, for determining lead trajectories for surgical planning based on the patient images and patient assessment information. The programs can also include ones usable for registering a lead model to a patient atlas, e.g., after the lead has been implanted. The cloud can further include programs used for planning stimulation programs, and for actually programming the implanted pulse generator (IPG). A smart phone 1316 can be used to access these programs. A stimulation bridge 1318, which can be embodied in a dongle, can interface between the IPG 1320 and the stimulation programming module for programming the IPG to cause the implanted leadwire to generate electrical pulses according to the program. Information concerning the effects of the stimulation can be obtained automatically and/or manually input, e.g., via a patient interface module, which can also be accessible from the cloud to update the analytics information. The effects information are correlated with the stimulation program set in the programming module and for which the program planning module generates estimated VOAs.

Data Export/Import

According to an example embodiment of the present invention, a same stimulation-related and/or anatomical atlas (patient-specific or non-patient-specific) data can be accessed via multiple computer terminals. For example, in an example embodiment, such data is saved to a file stored at a central location accessible from multiple computer terminals.

In an example embodiment of the present invention, such data can be shared with other users, e.g., as an attachment to a communication (e.g., an e-mail) or by providing the other user access to the centrally stored file. Such data often includes information that is specific to a patient and private. Accordingly, in an example embodiment of the present invention, the system includes an anonymization feature for stripping from the shared data any data that identifies the patients. For example, in an example embodiment, the system includes a soft or hard selectable button, in response to selection of which the system strips private data. For example, the system can be programmed to remove patient name, address, social security, etc. In an example embodiment, in response to selection of the anonymization button, the system outputs a list of types of data which the user can select to strip. In an alternative example embodiment, the system saves the information centrally with all of the data, and depending on permissions set for a user attempting to access the centrally stored data, either provides the data with the private information or provides a stripped-down version of the data.

According to an example embodiment of the present invention, the system is configured to transmit VOAs or other volumes in the form of centroids (e.g., center of mass of the volume), e.g., in combination with other elliptically based information, as further described below. In an example embodiment, volumes can be transmitted/opened in a CAD format. Volumes can be exported to other users in the reference frame of the patient for whom the volume was generated. Alternatively, the volume can be transformed to a common reference frame, e.g., a common atlas, and transmitted to other users in this generic form. In an example embodiment, the system is configured to export the VOA or other volume as a full 3D mesh of the volume.

In an example embodiment, the system is configured to export geometric primitives of the volumes, e.g., of the VOAs. For example, in an example embodiment, the system saves/transmits the parameters of a sphere or ellipse that best matches the VOA, which allows for the amount of data that is to be saved and/or exported to be scaled down. Such data can be sent, for example, in an Excel format, as a comma delimited file, as a text file, or as a CAD file. Providing the volume information in such forms can be beneficial to allow one to use third party applications not adapted to interpret/process the more intricate volume data the Guide software is configured to process.

For example, a volume, e.g., a VOA, can be saved/transmitted as a set of points in 3D space with information on how those points are connected. Alternatively, the volume can be saved as a combination of a centroid and, for example, a radius. The radius can be that which is determined to provide an ellipse that optimally overlaps the volume, e.g., with least combined difference of overlap and underlap to the volume or the smallest ellipse that covers all points of the volume. For example, the system can store a plurality of volumes, each as a row including the data {x, y, z, r}, where x, y, z represent a point in three-dimensional space at a center of mass of the volume and r represents the radius.

Figure 9:
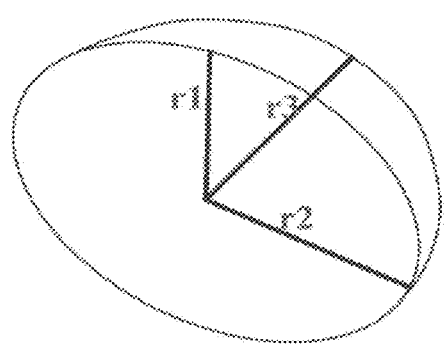
FIG. 9 illustrates components usable for representing an anatomical volume, according to an example embodiment of the present invention.

According to a variant of this embodiment, the system can include multiple radii to represent the volume, for example, to represent a three-dimensional ellipsoid. For example, three radii r1, r2, r3 can be used, each for a respective one of the x, y, and z directions, as shown in FIG. 9. In an example embodiment of the present invention, the system further provides additional data indicating an orientation of the ellipse in an atlas or anatomical image space. This is because the same ellipse can be orientated in a number of ways relative to the same anatomical space. In an example embodiment of the present invention, the orientation information is provided as any two of three angles. For example, a first angle can represent an angular offset from the superior-inferior line, a second angle can represent an offset from the anterior-posterior line, and a third angle can represent an offset from the medial-lateral line. Thus, each of the radii can be a radius drawn along one of those lines, and each angle can be a respective offset for a respective one of those radii.

Alternatively, geometric primitives other than radii and/or x, y, z coordinates can be used as an estimate of the volume. For example, a geometric primitive to be used for characterizing a sphere can be a diameter; geometric primitives to be used for characterizing an ellipsoid can be axes lengths; geometric primitives to be used for characterizing a hexagon can be side lengths; geometric primitives to be used for characterizing a pyramid can be a height, lower radius, upper radius, etc.

Other data can be provided to further define the volumes, e.g., warping parameters, such as an indication of an amount of warp, a direction of warp, etc.

In an example embodiment, a geometric volume can be represented by identification of elements, voxels, or nodes that are included or excluded, e.g., the system includes a standard format by which to present such information.

In an example embodiment of the present invention, a more precise volume can be saved/transmitted in an Excel, comma-delimited, or other similar format. For example, in an example embodiment, a volume can be represented using a first record corresponding to a volume includes a plurality of tuples, each tuple corresponding to a single point in two or three dimensional space, and a second record identifying each pair or triple of connected ones of the points. For example, the following record can be stored $\{x_1, y_1, z_1; x_2, y_2, z_2; x_3, y_3, z_3; \ldots \}$, where each x, y, z, combination is one point on a perimeter of the volume. The following additional record can be stored $\{1,2,3;3,4,5; \ldots \}$, where each combination of numbers identifies a respective combination of tuples that are connected. For example, "1,2,3" indicates that the point of tuple 1 is connected to the point of tuple 2 and to the point of tuple 3. If points of a two-dimensional volume are stored/transmitted, the second record may be in the form of, for example, $\{1,2;2,3;3,4; \ldots \}$, where each combination of numbers identifies a respective combination of tuples that are connected. For example, "1,2" indicates that the point of tuple 1 is connected to the point of tuple 2, etc.

Integration of Surgical Planning and Stimulation Programming Systems

Figure 14:
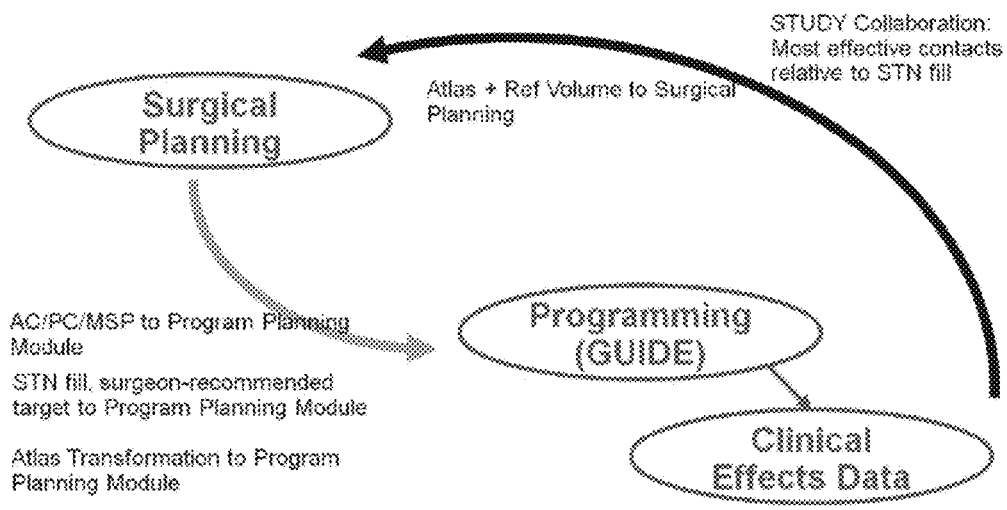
FIG. 14 illustrates a paradigm in which surgical planning, stimulation programming/planning, and analytics modules are integrated, according to an example embodiment of the present invention.

FIG. 14 illustrates a paradigm in which surgical planning, stimulation programming/planning, and analytics modules are integrated, e.g., by direct data export from one module to another or by saving of information in a cloud which the information is accessible by all of the modules. For example, the AC/PC/MSP (anterior commissure/posterior commissure/median sagittal plane) can be identified in a surgical planning system, and can be accessed by the programming module to program stimulation settings based on the identified anatomical markers. Similarly, a surgeon can select a target structure or other target volume, e.g., manually drawn, as a target for stimulation, which the program planning module obtains for use for finding stimulation parameters that are best for providing stimulation of the target region.

Similarly an atlas registration can be performed using the surgical module, and the registered atlas can then be used with the program planning module to accurately select stimulation parameters. In an example embodiment, for the atlas registration, the surgical planning system transmits an identification of a location of a relevant MR, an identification of a relevant CT, and a number matrix for transformation of the MR and CT information to yield patient atlas.

Pre-op lead location information and a pre-op CT can be provided to the stimulation programming module for use to determine the lead location, on which basis to select stimulation settings for stimulating a target volume. MER data of the surgical planning module can also be accessed by the programming module.

The programming modules can be used for selecting stimulation programs, and generating estimated volumes of activation. Further, the programming module can obtain clinical effects data associated with the VOAs corresponding to the implemented stimulation programs, on which basis analytics are performed, as described below. The analytics are used to refine target areas, and the information can be provided back to the surgical planning modules, for view therein by a user, e.g., a surgeon, to better select a target region for future surgeries.

Though not shown in FIG. 13, the surgical planning system of FIG. 14 can have access to the cloud shown in FIG. 13 to facilitate the described system integration.

Figure 15:
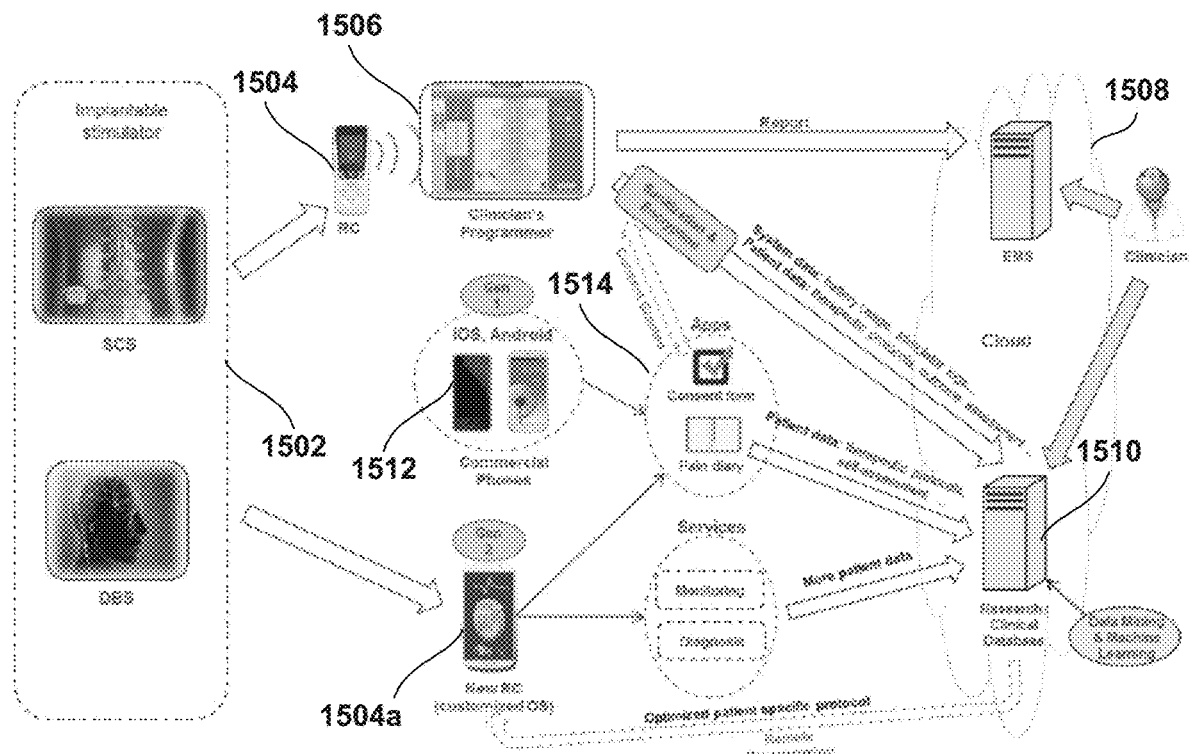
FIG. 15 is a further illustration of cloud integration of various modules, according to an example embodiment of the present invention.

FIG. 15 is a further illustration of cloud integration of various modules. A system can have any combination of the following components: an implantable stimulator 1502 (including, for example, a IPG and one or more leads); a remote control (RC) 1504, 1504a; a clinician programmer (CP) 1506, cloud or other central storage 1508 with a database 1510; and a smartphone 1512 or other computing devices that can access applications 1514 (Apps). FIG. 15 illustrates representative flows of data, information, and communication between these components including examples of the types of information that may flow. It will be understood that information flow, although exemplified in one direction in FIG. 15, can often flow in both directions between system elements.

A web-based platform has at least three advantages over a local device paradigm. First, fixed hardware platforms inevitably become obsolete as hardware changes occur. Such a scenario would not occur in a web-based platform. Second, a web-based platform would enable separation of client and server and allow deployment of algorithms to which terminals can gain access over time. Third, a web-based platform could dramatically aid online analysis.

The modules can include a Patient Data module, a Registration module, and a Patient Programming module. The Patient Data module allows the user to browse and select patient datasets. The Registration module then allows the user to select a pre-operative MRI dataset and a post-operative CT dataset. The user then can fuse these datasets and view the fused datasets either individually or in an overlay. In addition to fusing MR and CT datasets, the Registration module allows the user to automatically or manually determine the positions of stimulation leads from the post-operative CT images and also enable semi-automatic registration of the patient's MRI on to a standard Atlas. Once the lead positions are determined and registration is completed, the Patient Programming module allows the user to visualize areas of the brain activated in response to different DBS stimulation settings. Since these areas are depicted in the software in a reference frame that includes relevant atlas structures, the user can utilize the display as a guide for optimal choice of stimulation parameters.

These functionalities can be provided in a web-based system, which can include the following components: (1) a web-based front end through which the user will control the program, (2) a back-end server which will perform a significant portion of the computations required by the user, and (3) a back-end database to serve as a Laboratory Information Management System (LIMS). In an example embodiment, the front-end runs in at least one browser and has a secure connection to the back-end server.

Front End:

Patient Programming Module:

The Patient Programming Module allows the user to select DBS stimulation settings and depicts the corresponding VOA. In an example embodiment, the computations for generating the VOA are performed on the client. Alternatively, they are performed on the server with 3D models being pushed to the client. Either way, the system outputs VOAs and atlas structures for varying DBS settings. The system rotates Atlas and VOAs through (at least) a discrete set of angles to enable appreciation of intersections between the VOAs and atlas structures and changes of VOAs with varying parameters.

Registration Module:

This module allows scrolling through MR and CT datasets, fusion of MR and CT, auto-detection of leads from CT, and registration of MRI onto atlas. With respect to the registration, in an example embodiment, the AC-PC (anterior commissure-posterior commissure) is selected and an atlas is selected to match the atlas AP-PC to patient AC-PC. In an alternative example embodiment, there is a fully automated registration algorithm, e.g., using B-splines. In an alternative example embodiment, the system maintains a large database of patient population MRs, and the system finds the best match between the current patient's 3T MR and the database of 7T MRs (or the best few matches).

Patient Data Module:

This module allows users to see which datasets are available on the server. The user is able to select one pre-operative MR dataset and one post-operative CT dataset for further analysis. If the LIMS exists, patients can be selected based on their behavioral scores or any other criteria of choice. Users can also view behavioral measures, such as UPDRS scores as bar plots, and accelerometer readings as time series/power spectra.

Back End:

In an example embodiment, the back end has the ability to accept secure requests from the client and display available datasets, provide feedback slices of MR and CT when the user scrubs through the data, perform fusion when user selects one CT and one MR dataset from available list and to feedback fused MR and CT datasets, perform registration and feedback registered MR+CT and atlas structures to the client, and perform VOA calculation and feed the results back to the client.

Data Capture on the Remote Control (Patient Programmer)

A need in neuromodulation is to have some way to blind a patient as to whether the patient's device is on or off. This is helpful, for example, for clinical trials. This is difficult because the patient usually has a remote control that informs the patient of this information. Therefore, according to an example embodiment of the present invention, the remote control is provided with a clinical mode, where the remote creates the illusion as though the device is on, e.g., the user can interact with a user interface to raise or lower the stimulation amplitude and/or other settings, when really nothing is happening in response, although the remote gives the appearance as though the system is responding to the user's commands.

For example, referring to FIG. 1, a remote control 100 can include a display screen 102 including graphical information regarding parameters set in the IPG, including, for example, the pulse width 104, current amplitude 106, and power amplitude 108 of electrodes of an implanted leadwire controlled by the IPG. The display screen 102 can include additional information regarding the IPG, such as one or more representations of its battery power and life 110. The remote control 100 can include one or more buttons 112 via which the patient can input instructions to the IPG for modifying one or more of the settings. For example, the user can, in an example embodiment, select an electrode and input a desired amplitude setting, polarity, etc. for the selected electrode, e.g., by textual input, or by selecting an up or down arrow to raise or lower a setting. In an example embodiment, a graphical representation of an electric field 109 drawn about one or more graphical representations of respective electrodes can be shifted, e.g., using arrow keys, which is interpreted as an instruction to modify one or more settings to provide the shifted electric field. The remote control 100 can include other features for input of stimulation settings, for example, as described in the '330, '312, '340, '343, and '314 applications.

In an example embodiment, when the remote control 100 is in the clinical mode, if the user manipulates the input elements, e.g., buttons 112, of the remote control 100 to modify the settings of the IPG, the remote control 100 updates the graphical user interface (GUI) to reflect the input modifications, without the input modification instruction being implemented at the IPG. For example, the remote control 100 can refrain from responsively transmitting modification instructions to the IPG, or the remote control 100 can transmit the instruction, but the IPG can ignore the instruction. According to the latter embodiment, the IPG enters the clinical mode, while the remote control 100 is blind to whether the system is in a clinical or a regular mode. Although the instruction to modify the settings is not executed, the remote control 100 can display the modified setting, such as a modified pulse width, current amplitude, and/or power setting, and/or the location(s) of one or more of the displayed current fields, as though it had been implemented.

The remote control 100 can also modify the battery power and life representations 110 to reflect the modifications as though they had been implemented. For example, in response to instructions for modifications that when implemented would cause a change in the battery power and expected battery life, the remote control 100 may update the battery power and life representations to reflect such change, although the modifications are not implemented.

Additionally, in an example embodiment, where the IPG does not perform with the leadwire a stimulation, such that battery power of the IPG is not being used or is used at a very low rate, but the patient is led to believe in clinical mode that a stimulation program is being applied, the remote control 100 modifies the battery power and life representations 110 as though the stimulation program is being applied.

In an example embodiment of the present invention, in the clinical mode, the remote control 100 provides an output, e.g., a graphical, audible, or tactile output, warning of low battery power of the IPG, such that a recharge is suggested, in accordance with the indicated stimulation program, although the program is not being applied and the battery power is in fact not depleted.

In an example embodiment, the remote control 100 includes a charger for charging the IPG battery. For example, the remote control 100 can include a wire with a coil for inductively charging the IPG. In the clinical mode, where the IPG battery is shown to be at less than its actual charge level, and the user uses the remote control 100 in order to charge the IPG battery (although the battery might be fully charged), the remote control 100 may update the battery power and life representations 110 to reflect an increase in the battery power and remaining life, as though being increased from the low battery power and life indications.

Figure 2:
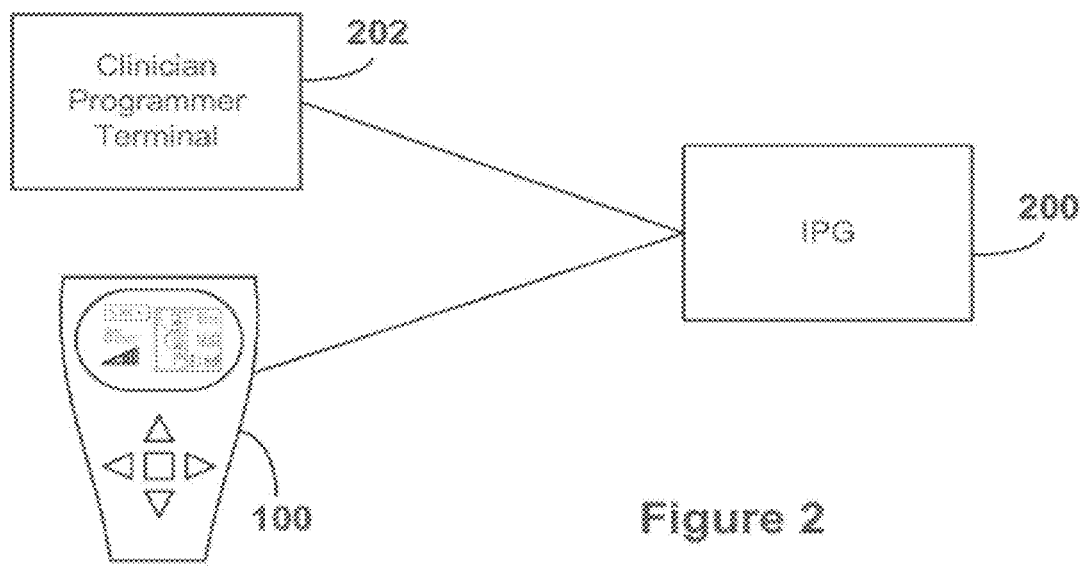
FIG. 2 shows connections between a remote control device and other system components according to an example embodiment of the present invention.

In an example embodiment of the present invention, as shown in FIG. 2, the remote control 100 communicates with the IPG 200 and also interacts with a CP (clinician programmer) terminal 202, e.g., a laptop or other computer terminal in which a clinician programmer application is executed.

For example, a user operating the CP terminal 202 can input upper and/or lower bounds of a parameter of the IPG 200, e.g., upper and lower amplitudes for a stimulation program. The CP terminal 202 can transmit, e.g., wirelessly, data to the IPG 200 for setting the upper and/or lower bounds within the IPG 200. The patient can operate the remote control 100 to set one or more stimulation parameters of the IPG 200. However, the IPG 200 ignores parameter settings received from the remote control 100 that are not within the upper and/or lower bounds set by the CP terminal 202. Alternatively or additionally, in an example embodiment, when the remote control 100 communicates with the IPG 200, the IPG 200 responsively notifies the remote control 100 of the restrictions set by the CP terminal 202, and the remote control 100 thereafter refrains from transmitting to the IPG 200 settings that do not comply with the restrictions, until the IPG 200 informs the remote control 100 of removal or modification of the restrictions.

Figure 3:
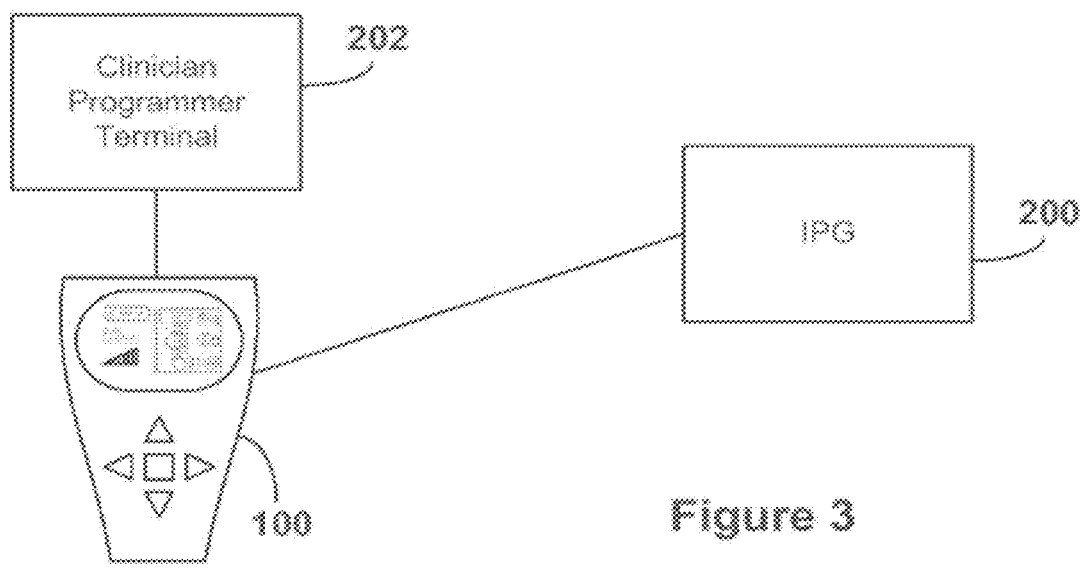
FIG. 3 shows connections between a remote control device and other system components according to another example embodiment of the present invention, aspects of the different illustrated embodiments being combinable.

In an alternative example embodiment, as shown in FIG. 3, the CP terminal 202 communicates restrictions concerning the stimulation settings to the remote control 100, and the remote control 100 refrains from transmitting instructions to the IPG 200 that do not satisfy those restrictions. For example, if the user inputs an instruction to set a stimulation amplitude to a level that is higher than an upper bound communicated by the CP terminal 202 to the remote control 100, the remote control 100 ignores the user input instruction, e.g., at least with respect to responsively transmitting an instruction to the IPG 200.

In an example embodiment, such bounds may be set in a clinical mode, such that the remote control 100 responds to a user input to modify a parameter to a level that is beyond that which is allowed by the instructions of the CP terminal 202 by accordingly modifying the GUI in the display screen 102, but refrains from sending instructions to the IPG 200 to set a parameter to the impermissible level, or, according to the embodiment described with respect to FIG. 2, the remote control 100 possibly sends the instructions, which the IPG 200 ignores according to the restrictions received from the CP terminal 202. However, as noted above, in an example embodiment, the IPG 200 can also communicate to the remote control 100 the restrictions set by the CP terminal 200. Additionally, in an example embodiment, the IPG 200 informs the remote control 100 that it is operating in clinical mode, and the remote control 100 responsively modifies its output as described above to provide the illusion of changes being implemented even though they are not being implemented.

The embodiment described with respect to FIG. 2 may be preferable over the embodiment described with respect to FIG. 3 so that if a new remote control is used, the CP terminal 202 need not resend the restrictions to the new remote control.

In an example embodiment, a clinician can put the device in a mode such that it goes on and off at various preset times, and the patient does not know when it is on or off. For example, the CP terminal 202 can send instructions concerning such a stimulation program to the IPG 200, which can, in turn, inform the remote control 100 of the stimulation program, e.g., which cannot be overridden by the patient via the remote control 100, or which can be overridden by the patient in only defined limited ways, e.g., for safety reasons. Meanwhile, the remote is configured to receive from the patient input indicating how the patient is doing. Such feedback may include input of a number on a predetermined scale. For example, the device outputs a reminder to input the information. So now clinical trial data can be obtained where information on how the patient is doing is periodically received, and the patient does not know when the device is on or off. Patient feedback may be time-stamped for subsequent clinical analysis.

Additionally, in an example embodiment, the device changes the program used to stimulate at various intervals, and the remote does not indicate to the patient which stimulation parameters are being used at that time. The patient then records over time how the patient is doing. Over time, the device learns which program is best for the patient by determining for which parameters the patient has been indicating the patient feels best. For example, the device can iterate through a number of settings for each electrode, gradually increasing the amplitude at a respective electrode contact of the leadwire, and continuously do so as long as the patient provides good feedback about that setting. In this example embodiment, the patient does have the ability to manually override the predetermined settings, for example, in case the device automatically sets a dangerous setting. Therefore, recorded feedback may include patient override requests.

In an example embodiment, there can be sensors that sense how the patient is doing. In addition to the patient manually entering how the patient is doing, the sensor information can be used to indicate how the patient is doing. Such sensors may include, for example accelerometers or other sensors that detect motor skill and/or cognitive functioning, for example, tremor (motor skill), dwell times (motor skill/cognitive), etc. The sensors may be integrated into the remote, the IPG or any other hardware that the patient carries.

The information on how the patient is doing and the related stimulation parameters can be stored at the central server.

In an example embodiment of the present invention, the preset stimulation program, whether including a single steady set of parameter settings, or including a plurality of sets of parameter settings that are implemented at different times, e.g., at different intervals, can be set in a clinical mode, as described above, where the GUI of the remote control 100 is modified to reflect changes entered by the patient, although such changes are not implemented. In an example embodiment, even in a clinical mode, the system may allow the user to override certain settings for safety reasons.

According to an example embodiment of the present invention, the system may be configured to perform a clinical study for testing various settings, including, for example, testing a response to an on-low setting at which a low power stimulation is applied, an on-high setting at which a high power stimulation is applied, and an off setting at which no stimulation is applied. In an example embodiment the clinical stimulation program includes cycling through the three (or more) settings one or more times at equal or varying intervals. As explained above, the patient can be blind to the changes, and the system can be configured to record information regarding the patient's condition at various points during the stimulation program, which information can be obtained from user input and/or from sensors.

In an example embodiment of the present invention, the system may include an electronic diary ("e-diary") feature for recording a log of time-stamped patient condition information, and for recording time-stamped information concerning the stimulation settings, so that the patient condition information can be associated with particular stimulation settings. Certain of the recorded information can pertain to factors that are not a result of the stimulation settings, e.g., which medication(s), if any, the patient is taking. Other of the patient condition information can be associated with a combination of the stimulation settings and the medication(s) the patient was taking at the time associated with the patient condition information.

In an example embodiment of the present invention, for obtaining patient condition information, medication information, etc., the remote control 100 includes user input hardware and/or software controls via which the patient can enter information. In an example embodiment, the remote control is configured to receive input from the patient of entry of a number on some number scale, e.g., 1-10, of how the patient is feeling. In an example embodiment of the present invention, the remote control 100 includes a "good" button and/or a "bad" button by which the patient can generally indicate whether the patient generally feels good and/or bad. In an example embodiment of the present invention, the remote 100 includes soft and/or hard buttons (or check boxes, radio buttons, etc.) for predetermined significant events, such as, for example, falls, seizures, etc., which the patient can select when such an event occurs. The system can record a time-stamped entry in the e-diary noting the occurrence of the event indicated by the selection of the corresponding event input.

In an example embodiment, the remote control 100 stores the e-diary information locally in a long-term storage of a memory device of the remote control 100. In an example embodiment, the remote control 100 alternatively or additionally transmits the e-diary information to the IPG for storage therein. In an example embodiment of the present invention, the e-diary information is alternatively or additionally uploaded to a central server, e.g., as discussed above under the "Cloud Data Management" section.

As noted above, in an example embodiment the system is configured to record a time-stamped log of the stimulation settings. In an example embodiment, the IPG records time-stamped stimulation settings at predetermined intervals. In an alternative example embodiment, the IPG records time-stamped stimulation settings responsive to a change to the stimulation settings. In an example embodiment, after recording initial settings, subsequent settings are recorded as a change to the immediately preceding settings.

In an example embodiment of the present invention, the system correlates respective portions of the patient-condition information to respective settings based on the time-stamps, and automatically modifies settings based on the correlation. For example, in an example embodiment, the system detects a trend, e.g., that with increase of a certain parameter between a first time and second time, the patient condition has deteriorated, and therefore modifies the settings, e.g., in a reverse direction in response to a detected deteriorated condition and/or further in a same direction in response to a detected improvement in condition.

In an alternative example embodiment, or additionally, the system outputs a report of the effects of the settings on the patient condition. For example, in an example embodiment, the system outputs a report that an increase or decrease of parameter 'x' has been detected to be associated with a deterioration or improvement of condition 'y'.

In an alternative example embodiment, or additionally, the system outputs a timeline covering a time period including some or all of the time-stamped times and further outputs against the timeline (a) a graph representing changes to one or more patient conditions indicated by the patient-condition information, and (b) identifications of the settings prevailing at different times of the timeline.

VOA Selection for Target Volume

A target volume can be selected, e.g., by a user or by the system, e.g., based on clinician input, the patient's information (such as a patient disorder, patient history, etc.) population information (such as learned information from one or more other patients), therapeutic goal, etc. In an example embodiment of the present invention, the system outputs suggested stimulation settings and/or outputs a graphical VOA corresponding to suggested stimulation settings for such a target volume.

Figure 4:
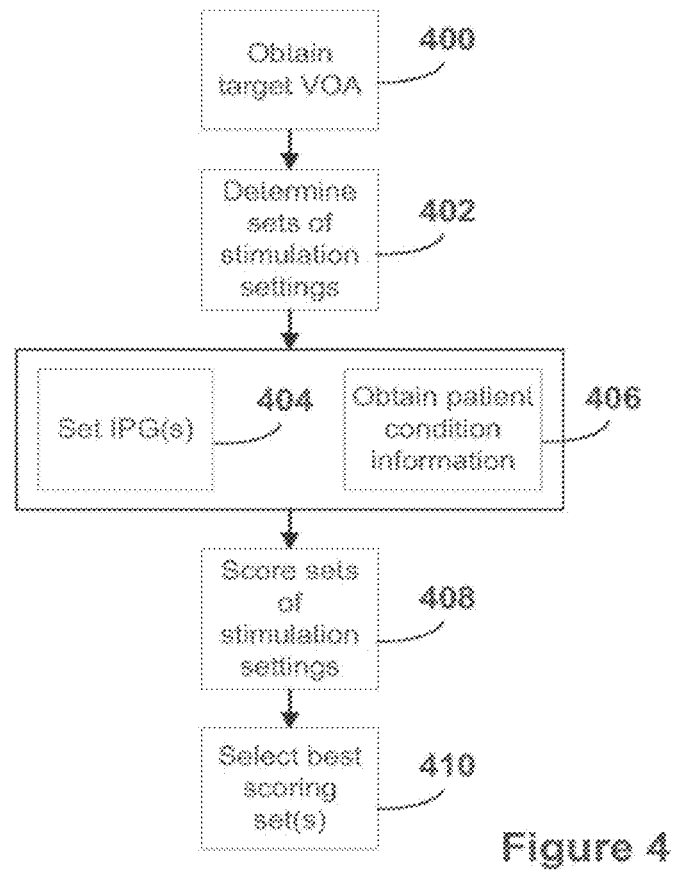
FIG. 4 is a flowchart that illustrates a computer-implemented method of refining target volume selection, e.g., over time, according to an example embodiment of the present invention.

Referring to FIG. 4, at step 400 the system obtains a target volume. At step 402, the system determines a plurality of sets of stimulation settings that provide VOAs considered similar to the target volume. The system can perform such a determination according to a predetermined one or more conditions, such as a degree to which a VOA must overlap the target volume and/or a maximum amount by which the VOA can spill beyond the boundaries of the target volume. In at least some embodiments, the conditions can be selected and values chosen by the clinician or other user. At step 404, the system sets the IPG of one or more patients, e.g., for whom the target volume (or a similar target volume) is obtained, to test some, or each, of the plurality of sets of stimulation settings. The settings may be tested on a single patient, e.g., the particular patient for whom the system will output the suggested optimal settings in view of the obtained target volume, or across a patient population. According to an example embodiment, where the settings are tested across a patient population, different ones of the sets of stimulation settings can be tested in parallel. According to an example embodiment, where the settings are tested by applying the sets of stimulation settings to a single patient, the system cycles through a program in which different sets of the stimulation settings are applied in a sequence over time, different ones of the sets being applied during different intervals of the program.

At step 406, the system obtains patient condition information for the tested settings. Steps 404 and 406 may be performed concurrently. That is, while a patient is stimulated by a set of stimulation settings, the system is configured to obtain information concerning the patient's condition, e.g., via patient input or by sensor signals, as described above. The information and settings can be time-stamped. The condition can include therapeutic effects, side effects, patient ratings, and the like, or any combination thereof.

In an example embodiment, for each of the patients on which the sets of stimulation settings are tested, the system associates the patient condition information with the set of stimulation settings applied to the respective patient for whom the respective patient condition information was obtained, the association being based on a determined correspondence of the timestamps of the patient condition information and the applied set of stimulation settings, as explained above.

In an example embodiment, at step 408, the system assigns a score to each of the sets of stimulation settings based on the patient condition information associated with the respective set. For example, different weights can be applied to different types of patient condition information to calculate an overall score. According to an embodiment in which the sets of stimulation settings are tested across a patient population, the system can test a same one of the sets on multiple patients. In an example embodiment, the system calculates an average score of the scores calculated for each patient for whom the set of stimulation setting was applied.

At step 410, the system may compare the calculated scores and select a predetermined number or percentage of the best scoring, e.g., the 3 highest scoring or the single highest scoring, tested set(s) of parameter settings as candidate parameter settings (and associated VOAs) to output as suggestions for a patient for whom the same or similar target volume is selected.

The target volume selection and/or the selection of suggested settings can be performed on any computing device, e.g., a CP terminal.

In an example embodiment of the present invention, the sets of settings can be tested in a clinical mode during which the patient is blinded to the settings.

Programming Based on IPG Efficiency

It is possible for a plurality of different sets of stimulation settings to result in the same or similar VOAs, where certain ones of the sets of stimulation settings are more electrically efficient than others of the sets. For example, similar tissue activations may be obtained by varying the electrical amplitude and pulse width. For example, first settings have a high amplitude and a short pulse width can be equivalent or approximately equivalent to second settings having a lower amplitude but a longer pulse width. For example, equivalence can be measured in terms of power or total current delivered or by any other relevant measure, including the strength/duration curve discussed below, and "approximately equivalent" can be, for example, a variation of 1, 2, 5, or 10 percent.

In an example embodiment of the present invention, the system can in step 402 select a plurality of electrically equivalent settings that differ in their respective amplitudes and pulse widths. It is noted that although such sets of settings may be considered electrically equivalent and/or calculated to produce equivalent or substantially equivalent VOAs, it may nevertheless occur that the different sets of settings produce different clinical effects. Therefore, in an example embodiment, the system tests these equivalent sets at steps 404 et seq.

In an example embodiment of the present invention, the system also assigns a weight to electrical efficiency for the calculation of the scores at step 408.

In an example embodiment of the present invention, the system finds a plurality of sets of electrically equivalent stimulation settings using a strength/duration curve. For example, in an example embodiment, at step 402, the system determines a set of stimulation settings that is estimated to produce a VOA that best fits the target volume, and then finds other sets of stimulation settings that are electrically equivalent to the determined set of settings based on the strength/duration curve.

According to an example embodiment of the present invention, the system uses a strength/duration curve that relates to the discharge of an IPG. In an example embodiment, a device is programmed, e.g., automatically, to use the least amount of energy to fill the target volumes based on the strength/duration curve. In an example embodiment, the efficiency of the settings is one of a plurality of factors contributing to a score on whose basis a set of settings is selected, as described above, where, all else being equal, greater efficiency results in a higher score.

In this regard, according to an example embodiment, programming settings are automatically adjusted towards a target volume specified by a user (or otherwise selected). The visualization system is configured to, based on the specified target volume, test settings that use the lowest power consumption while reaching the specified target volume. In an example embodiment, the system also tests settings that yield volumes that approximate the target volume (e.g., slightly larger or smaller than the target volume). Additionally, in an example embodiment, the testing of such settings can be performed during the clinical mode, so that the optimal settings (in terms of a combination of therapeutic effectiveness and power consumption) is obtainable with the aid of feedback from a blinded user.

Figure 5:
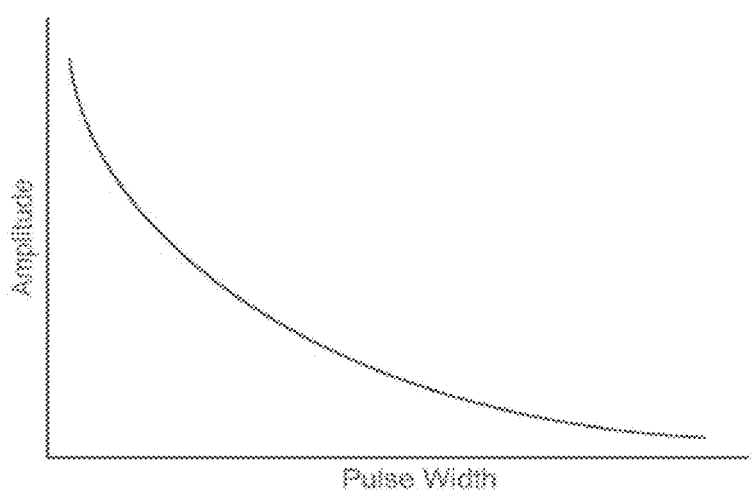
FIG. 5 is an example strength/duration curve plotting different combinations of power and pulse width values estimated to provide equivalent stimulation, according to an example embodiment of the present invention.

FIG. 5 shows an example strength/duration curve, where the ordinate represents the amplitude and the abscissa represents the pulse width, where the plotted points are all estimated to produce substantially equivalent volumes of activation. The graph shows that the higher the amplitude, the shorter the required pulse width for producing substantially the same volume of activation. That is, a fiber is expected to fire based on a combination of amplitude and duration of the stimulation at that amplitude, so that the higher the amplitude, the shorter the required duration for causing the fiber to fire.

According to an example embodiment of the present invention, for a selected VOA, the system plots the strength/duration curve of values that are estimated to produce the selected VOA, and selects the most efficient of the pairs of values, e.g., assuming all other factors being equal (as noted above, other factors may result in selection of a set of values different than those of the most efficient pair).

For example, the system can obtain a target volume, e.g., user-selected or automatically selected. The system then determines one or more closely matching producible VOAs. The system is configured to select, for each of one or more of such VOAs, a most energy efficient pair of amplitude and pulse width values to produce the respective VOA. For example, where a remaining battery power is 3.7 v and a required amplitude is more than 3.6 volts, the system can use capacitors to double the voltage to 7.4 v. If less than 7.4 v is required, the system can burn off the difference between 7.4 v and the required voltage. For example, if 4 v is required, the system can burn off 3.4 v, which is inefficient. Accordingly, for the 4 v requirement, the system can determine from the strength/duration curve whether there is a more efficient pair of settings. For example, the system might determine that the same VOA is producible with a longer pulse width at 3.5 v.

SFM Analytics

Example embodiments of the present invention pertain to determining a target volume by analysis of VOAs for a plurality of patients.

According to an example embodiment of the present invention, a system can include program code for providing visualization features to output graphical representations of estimated VOAs, e.g., about a representation or image of an implanted leadwire and/or overlaying a model or image of a patient anatomy. The system can include code by which user, e.g., clinicians or patients, can test various settings estimated to produce such VOAs. The system can also include analytics code for determining a target volume, e.g., based on such VOAs tested by the users.

In an example embodiment of the present invention, the system includes features for facilitating the sharing by users of target volumes the different users have selected. In an example embodiment, the system includes features by which users can share data, such shared data being subjected by the system to analytics to determine optimal target volumes and/or optimal stimulation settings and corresponding VOAs.

Systems Configurations:

In an example embodiment of the present invention, the SFM analytics features are provided as part of a stand alone visualization system. For example, A Guide system can be used to modify/test parameter settings corresponding to VOAs and/or side effect volumes (volumes where stimulation is preferably avoided), and/or to set target volumes, which VOAs, side effect volumes, and/or target volumes can be transported to a separate analytics system on which analyses can be run. In an alternative example embodiment of the present invention, the SFM analytics features are provided in a Guide system including the clinician programmer features by which to program the settings of the IPG, such that the analytics by which to find optimal settings is conveniently on a system used to actually program the implanted device.

According to an example embodiment of the present invention, analytics information and input for performing analytics can be stored remotely via a cloud/internet-based system. In an example embodiment, the data from many systems, e.g., workstations operated by many users, can be stored centrally, and the centrally stored data and/or the resulting analytics information can be accessed by a plurality of users of networked systems.

In an example embodiment, the analytics features are provided in a software package that users can load onto the users' computers. Alternatively, the analytics features can be provided as a web-based application.

In an example embodiment of the present invention, the system is configured to allow a user to limit access to the data associated with the user, e.g., data created by the user or about the user, to only certain users (e.g., only one or more certain specified users or only users of one or more certain specified user groups) or to only certain systems (e.g., only via the Guide system). For example, the system can require entry of a user ID by which the system determines whether a user is authorized to access such restricted data.

It is noted that the analytics software and the input and/or output data can be at different locations.

Analyses of the SFM Analytics:

1. Population Overlap:

According to an example embodiment of the present invention, the SFM analytics system obtains as input a group of VOAs from a population of patients, where each VOA is associated with a measure of effectiveness, and the SFM analytics system determines a target volume based on the input information. For example, a collection of VOAs can form a group to be subjected to the analytics calculations where there is a clinically significant commonality between the VOAs of the collection. For example, VOAs of patients who share a certain diagnosis, e.g., the patients all have Alzheimer's disease, can form a clinically significant group for analysis to determine a target volume for treating Alzheimer's disease. Another or alternative significant commonality can be that the VOAs are associated with similar anatomical locations at which the stimulation electrode is implanted.

According to an example embodiment, the system is configured for a user, e.g., a physician, to manually create a group of VOAs to be used as input to analytics functions. For example, a physician might notice that a number of VOAs of stimulation settings applied to one or more patients provided excellent results, and the user can form a group for such VOAs. A single VOA can be a part of multiple groups.

In an example embodiment, for the analysis of a group of VOAs, the system places all of the VOAs in a common spatial reference space. For example, the system is configured to transform one or more, e.g., all, of the VOAs into a common atlas space. This may be required for example where the VOAs were obtained for different patients whose anatomical makeup varies.

The system is configured to determine where the VOAs of the common reference space spatially overlap for determining a target volume. For example, the system can output a combination of a collection of points, e.g., voxels, that belong to all or a threshold number or percentage of the VOAs of the group as a target volume. In this regard, VOAs each encompass a collection of points, e.g., voxels. According to an example embodiment, the system provides a user interface configured for user interaction therewith to input the threshold number or percentage.

Alternatively, the system can perform more complex calculations for finding voxels of significance shared by some of the group of VOAs, the combination of voxels of interest forming a target volume.

For example, in an example embodiment, the system is configured for obtaining ratings for each of the group of VOAs, e.g., one or more ratings for some characteristic, e.g., therapeutic effect, side effect, or how well it helped the patient with respect to some score. For example, clinicians can input into the system a rating on how well the patient is doing against some standardized scale.

The system is configured to assign a greater weight to those VOAs associated with better scores, e.g., the greater the score, the greater the weight. For example, the system can weight each point, e.g., voxel, within a VOA by the VOA's score. Then the system calculates for each of the points within any one of the group of VOAs, a respective score based on the combined weighted scores of the point across all VOAs of the group that include the respective point. For example, the system can sum the scores for each of the points. Alternatively, the system can average the scores for each of the points. According to the latter embodiment, the system also takes into consideration the number of VOAs in which the point is included. For example, a score of 0, a negative score, or some other value can be assigned to a point for a VOA in which it does not appear. Alternatively, the number of VOAs of the group in which the point is included can be considered as a separate factor in the calculation. According to an example embodiment of the present invention, the system compares each point's value to a threshold, and includes a point as part of an output target volume if the point's score meets the threshold. According to an example embodiment, the system provides a user interface configured for user interaction therewith to input the threshold score. According to an example embodiment of the present invention, the system selects a threshold number or percentage of highest scoring points as the target volume. According to an example embodiment, the system provides a user interface configured for user interaction therewith to input the threshold number or percentage.

According to an alternative example embodiment of the present invention, the above described thresholding can be performed to produce a volume which the system can subject to further calculations from which to select a target volume for output.

2. Group Comparisons:

In an example embodiment of the present invention, the system is configured to compare different groups of VOAs to determine target volumes of stimulation and/or volumes to be avoided, e.g., so as not to produce an unwanted side-effect. VOAs can be associated with respective therapeutic effects and/or side effects, including by degree of severity. For example, such associations can be based on user input provided using user interfaces such as those described for example n U.S. patent application Ser. No. 14/212,730, filed Mar. 14, 2014 and U.S. Prov. Pat. App. Ser. Nos. 61/793,773 filed Mar. 15, 2013 and 61/830,855 filed Jun. 4, 2013, the entire content of each of which is hereby incorporated by reference herein. Effects, associated with the VOAs, can also be obtained based on sensor information obtained during stimulation or in a period immediately following the stimulation. In an example embodiment, the associated effects are used for obtaining relevant volumes on which basis to generate new target volumes and/or side effect volumes.

For example, a first collection of VOAs associated with a certain side effect can form a first VOA group and a second collection of VOAs not associated with the side effect can form a second group. The system can automatically create these groups. Alternatively, a user can manually form the groups and input an instruction to the processor to perform a comparison. Similarly, the system and/or the user can select certain therapeutic effects as the characteristic by which to group VOAs. For example, an improvement in motor skill or a motor skill score can be set as a therapeutic effect by which to group VOAs.

The system is configured to transform the VOAs to a single common atlas space and find an area included in the group associated with the side effect (or therapeutic effect) and not included in the group that is not associated with the side effect (or therapeutic effect), and output the area, e.g., in relation to an atlas space, as an area that should not be stimulated. According to an example embodiment, more than one side effect and/or more than one therapeutic effect can be combined for the groupings, e.g., as a logical OR (e.g., any VOA associated with any one or more of certain specified side effects or therapeutic effects) or as a logical AND (e.g., any VOA associated with the combination of specified side effects or therapeutic effects). According to an example embodiment, the system is configured for use of a combination of side effect and therapeutic effect information for grouping VOAs in analytics for selecting a target VOA, by combining therapeutic effect areas and subtracting therefrom the side effect areas. According to an example embodiment of the present invention, the system provides a user interface configured for user interaction therewith to input a threshold degree of the side effect and/or therapeutic effect required for consideration of the respective VOA as part of the group.

Alternatively, a more complex calculation can be used to determine the points of the area to be avoided. For example, each point can be individually scored based on a combination of scores of all VOAs of the group associated with the side effect and in which the respective point is included, e.g., where the score for a point within a VOA depends on the severity of the side effect for that VOA. In an example variant of this embodiment, the system first finds which areas are included in a threshold number and/or threshold percentage (e.g., 100%) of the VOAs associated with the side effect and not included in a threshold number and/or percentage (e.g., 100%) of the VOAs not associated with the side effect. For voxels in the identified area, the system assigns respective scores based on the severity of the side effect for the VOAs in which the voxel is included. Alternatively, for each voxel, the system assigns a score based on a combination of those VOAs associated with the side effect an in which the voxel is included and of those VOAs not associated with the side effect. For example, inclusion in a VOA associated with the side effect can contribute to a higher side effect score, the extent by which the score is raised being dependent on the quantified severity of the side effect with which the VOA is associated; and inclusion in a VOA not associated with the side effect can contribute to a lowering of the score of the voxel. The system includes those points whose combined score meets a predetermined threshold, or a threshold number or percentage of points sorted by score, as the volume to be avoided.

Similarly, in an example embodiment of the present invention, where a benefit is associated with a first group of VOAs and is not associated with a second group of VOAs, the system finds the points, e.g., voxels, that are included in the VOAs of the group associated with the benefit and not included in the group that is not associated with the benefit, or scores points by the extent of their inclusion in one group over the other group, as described above, to output the combination of such points as a target volume.

According to an example embodiment, the system can, based on the VOAs of the patient population and their corresponding clinical effects, determine on a voxel-by-voxel basis, which voxels contribute to a certain effect, and combine those voxels into a target or side-effect volume. For example, if a voxel is included equally in both VOAs associated with a particular clinical effect and VOAs not associated with that clinical effect, then the voxel can be considered not to statistically significantly contribute to the particular effect. On the other hand, if a voxel is included statistically significantly more in VOAs associated with the effect than those not associated with the effect, then the voxel can be treated as being one that helps contribute to the specified effect when stimulated.

According to an example embodiment, the patient population VOAs and their effects can be used to construct electric field maps on a voxel-by-voxel basis with corresponding scores, for example, as described in U.S. patent application Ser. No. 13/600,855 filed Aug. 31, 2012, which is incorporated herein by reference in its entirety, to obtain a value for each voxel with respect to the specified effect.

According to an example embodiment, the system is configured to generate a probability voxel map that maps the probability that stimulation of each respective voxel will contribute to the specified effect, the system then selects all voxels whose probabilities meet a predetermined or user-input threshold probability, and the system then draws a three-dimensional surface outline around all the voxels meeting the threshold which are at the extremities to form the target or side effect volume. In an example embodiment, with further information concerning the leadwire location, the system is configured to output the stimulation parameters for stimulating the thus generated target region or for avoiding the thus generated side effect region.

In an example embodiment, a physician inputs desired therapeutic effects vs. side effects. Those therapeutic effects and side effects are weighted and overlaid/summed. A 3D voxel map is generated. A lead trajectory is placed in this space. Possible VOAs based on that lead trajectory are predicted and scored. The best score, weighted against needed settings, is chosen, and final settings proposed. For example, for each VOA/contour, map to a field, then inverse from field to programmed amplitude/pulse width settings. To choose a VOA, use sphere on radius r, placed along lead at spacing dx, and choose location x for sphere with maximal score.

3. VOA Steering Based on Clinical Effects/Indications/SFM Analysis:

According to an example embodiment of the present invention, the system provides a user interface for input of desired therapeutic effects and/or undesired adverse side effects to be considered, e.g., in the form of a questionnaire. Once the questionnaire is completed and submitted, e.g., by the press of a "submit" button, the system outputs a suggested set of stimulation parameters corresponding to a VOA and/or output the suggested VOA. For example, the system analyzes prior VOAs, e.g., as explained above, to determine the regions associated by the correct VOA corresponding to the indicated effects. According to an example embodiment, the system also provides for alternatively receiving input of indications of a patient, and the system finds the VOAs of the patient population corresponding to stimulations performed for other patients with the indicated indication(s), and outputs the overlapping (or other combination) VOA regions. According to an example embodiment, the system is configured to receive as input a set of indication(s) and clinical effect(s), and use the combination to filter the VOAs for determining and outputting a target volume.

According to an example embodiment, the system includes an input device such as a dial, as a hardware component or as a soft input device displayed as a user-interactive graphical component in a user interface, by which the user can input a change in a desired clinical effect or input a degree to which to consider an adverse effect to be avoided. For example, the user can turn a dial that is associated with tremor to indicate the degree to which the recommendation of a target stimulation location should be based on obtaining the desired therapeutic effect of reducing tremor.

In response to user interaction with the input device, e.g., in response to the user turning the dial, the system outputs the next closest program to result in that input change. The change in program for the desired change in clinical effect can be with respect to location of stimulation, pulse width, frequency, amplitude, etc.

An adjustment in some parameters to obtain a greater degree of the indicated therapeutic effect can result in an increase of adverse effects. Thus, in an example embodiment, the system determines the nearest VOA to result in the increased indicated therapeutic effect without the increase in the adverse side effect, or, where no such VOA exists, the one with the least increase in adverse side effect. Accordingly, in an example embodiment, the system finds the VOA closest to the VOA associated with the current settings that is also associated with the desired effect and not associated with the adverse effect. The system then outputs the program settings associated with the VOA closest to the VOA associated with the presently indicated stimulation settings, or, according to an alternative example embodiment, the VOA associated with the settings most similar to the presently indicated settings, where the modified settings produce the indicated desired change in clinical effect.

According to an alternative embodiment, the system determines the VOA for producing the greatest amount of the indicated desired change, determines a trajectory of possible VOAs between the one corresponding to the presently indicated settings, and, as the user turns the dial, the system outputs those VOAs and/or corresponding stimulation parameters, in succession until the optimal VOA is reached. According to an example embodiment, the system is configured to output a visual of the VOA path from the current location to the optimal location. For example, the system simultaneously outputs the current and optimal VOAs, as well as those in between, each for example being demarcated by a respective outline. In an example embodiment, as the user turns the dial, a different one of the displayed VOAs in the path is highlighted, and its associated parameters displayed.

Thus, for example, a presently set stimulation program is defined (partially) by amplitude, pulse width, rate, and location of stimulation pulses. A control, such as a dial, is provided for a corresponding effect or symptom. For example, a dial can be provided for tremor control. As the user turns the dial, the system auto-adjusts the parameters, e.g., auto-adjusts the amplitude setting, to gradually evolve the VOA corresponding to the current settings to the VOA associated with optimal tremor control, with each incremental turn of the dial moving the VOA another step along a tremor improvement path that extends from the current VOA location to that corresponding to the optimal tremor control.

Figure 11:
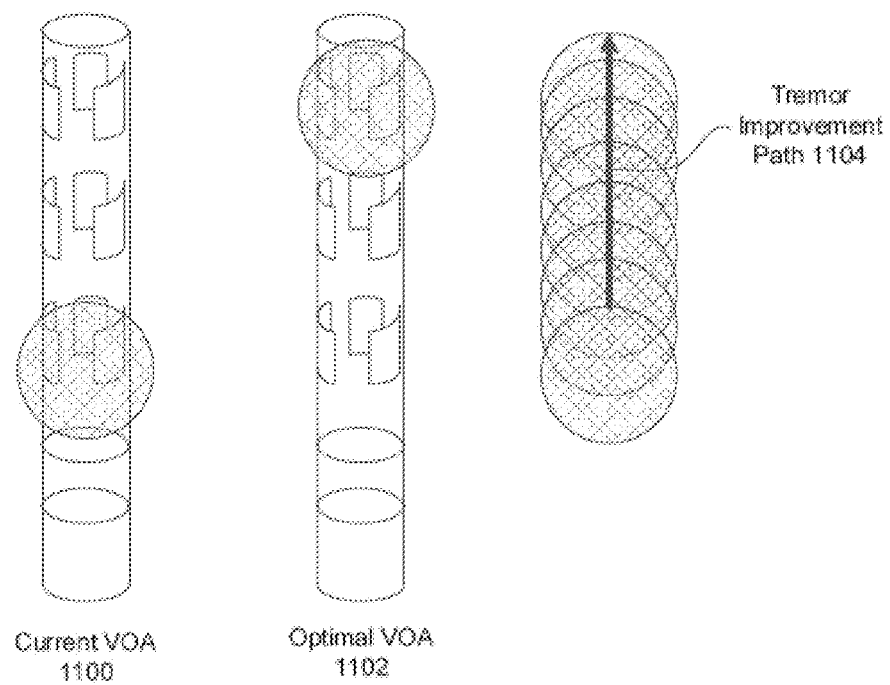
FIG. 11 illustrates an example of a trajectory between a current VOA and an optimal VOA, according to an example embodiment of the present invention.

FIG. 11 shows an example current VOA 1100, an Optimal VOA 1102 for improvement with respect to tremor, and a tremor improvement path 1104 outlining a trajectory from the current VOA 1100 to the Optimal VOA 1102.

Intermediate locations along the path can be associated with adverse side effects. According to an example embodiment, the system is configured to output warnings when intermediate VOAs are associated with causing adverse side effects. In an example embodiment, if multiple trajectories can lead from the current VOA to the optimal VOA, for tremor control for example, the system is configured to select the trajectory that avoids VOAs associated with adverse side effects, or that entails fewest VOAs associated with adverse side effects (even though the trajectory is not the shortest of the trajectories). According to an alternative example embodiment, the system is configured to skip over VOAs associated with any adverse side effects, or alternatively VOAs associated with severe side effects.

According to an example embodiment, the system is configured to alternatively or additionally perform the reverse, where the user inputs a stimulation program, and the system determines, based on the VOAs of the patient population and their corresponding indicated clinical effects, the expected therapeutic and/or adverse side effects of the indicated program. The system then outputs the expected clinical effects.

According to an example embodiment, in addition to outputting the expected clinical effect, the system is also configured to determine and output expected effects with certain slight modifications to the stimulation parameters. For example, in an example embodiment, the system outputs a message stating that if the stimulation is shifted a bit higher or rotationally around the leadwire by a certain number of degrees in a particular rotational direction, etc., then a particular specified change in clinical effect would be obtained. In an example embodiment, the system limits such output to minor changes, e.g., movement of the stimulation up to a certain distance upward or downward, or a certain number of degrees around the leadwire, or a certain threshold additional or lesser distance radially outward from the leadwire, etc. Alternatively, the system outputs the next expected change in effect for each of one or more of such changes regardless of the extent of the change, e.g., the next change in effect expected with a shift of stimulation upward regardless of the amount of such upward shift. The system or user may define the size of the minor change and may be, for example, a change of 1, 2, 5, 10 percent or more in the stimulation parameter.

According to an example embodiment of the present invention, a user can use a user interface of the system to steer stimulation, for example as described in U.S. patent application Ser. No. 14/011,836 filed Aug. 28, 2013 and/or in U.S. Prov. Pat. App. Ser. Nos. 61/693,866 filed Aug. 28, 2012, 61/699,135 filed Sep. 10, 2012, 61/699,115 filed Sep. 10, 2012, and 61/753,232 filed Jan. 16, 2013, the contents of all of which are hereby incorporated by reference herein in their entireties. In an example embodiment, as the user shifts the stimulation, the system checks the patient population VOAs to determine whether the steered change shifts the VOA estimated for the new steered settings towards a location associated with an adverse effect, in which case the system outputs a warning signal, e.g., visually, haptically, and/or aurally. For example, according to an example embodiment, a signal is gradually increased as the VOA is steered closer to, or to cover more of, the area to be avoided.

4. Group Analysis Considering Biological Networks:

The body includes various biological circuitries that biologically relate various parts of the body to each other in various respective ways. For example, as described in U.S. Prov. Pat. App. Ser. No. 61/904,248 filed Nov. 14, 2013, the entire contents of which is hereby incorporated by reference herein in its entirety, stimulation of one anatomical region can cause an effect in another anatomical region. Thus, according to an example embodiment, where there are VOAs grouped, for example by similar therapeutic or side effect regions, the system is configured to, for one or more particular biological circuitries, determine an overlap (if any) by a significant number of the VOAs with a shared component of the considered biological circuitry for generation of a target or side effect biological component with respect to stimulation. For example, in an example embodiment, the system is configured to determine whether a threshold number or percentage of VOAs that are associated with a particular therapeutic effect or side effect overlap a shared neurological fiber (even if the VOAs are in non-overlapping anatomical regions), and if so output an indication of that biological fiber as a target fiber or a fiber to be avoided (depending on whether it is associated with a therapeutic effect or adverse side effect). In fact, all of the features described herein with respect to determination and output of target or side effect volumes can also be used for determining and outputting target or side effect biological structures such as neurological fibers (for example, instead of returning a target volume in response to the input indications and/or clinical effects to be considered, the system can return a target of one or more fibers).

According to an example embodiment, the system uses a combination of region overlap and biological circuitry overlap for generation of a target volume or side effect volume. For example, the system generates the volume based on anatomical region overlap of the volumes, but only those volumes which overlie a shared biological component of a considered biological circuitry are grouped into a new target or side effect volume. For example, if neurological fibers are considered, then the VOAs associated with a same, for example, therapeutic effect are combined to form a new target volume conditional upon that they both overlie the same neurological fiber (of the respective patients with which they are associated).

According to an example embodiment of the present invention, the system displays putative functional subdivisions of a relevant anatomical region, e.g., the STN, and the putative connections between the anatomical region, e.g., the STN, and other regions, e.g., the pallidum, pallidum and thalamus, thalamus and cortex etc. When a VOA is activating a particular part of the STN, the system lights up corresponding nodes along the circuit and pathways within the biological circuit. In an example embodiment of the present invention, the system provides the display in a user interface in which a user can click the pathways, in response to which the system displays links to literature discussing the relevant biological connections. In an example embodiment, the system provides this information in a wiki in which the plurality of users of the system can provide additional source and explanatory information concerning the biological connections.

In an example embodiment of biological network/circuit analytics, fibers can be stimulated at different locations along some fiber(s). System knows that two points or structures are in some biological circuit or different points along the same fiber tract, and thus related and may have the same primary effect (perhaps with different secondary effects). For example, when planning an implantation and stimulation target, if the clinician desires to stimulate target A, but it is not possible (for example, other structures are in the way of target A), a target C that produces the same primary effect can be used and, therefore, implant in target C.

As another example, after implantation, the clinician desires to stimulate target A, but cannot because the lead is not in the necessary location, a target C that produces the same primary effect can be used and, therefore, program stimulation towards C. In these examples, the analytics determine that targets A and C have been shown to produce the same (or similar) effect, although they are spatially non-overlapping. Target volumes often reduce to a point but with, for example, DTI data, target volumes can reduce to a line.

5. Group Analysis Considering Biological Signals:

There are many types of brain signals corresponding to respective brain states, including for example, electrophysiological brain states. Examples of such signals include MER and Local Field Potential (LFP). Such signals can be location specific, e.g., to particular parts of the brain. Similarly, components in medical images can correspond to respective brain states, and therefore medical images, such as, for example, fMRI, PET and SPECT, also correspond to respective brain states. Such brain state data can be obtained and associated with patients and their respective VOAs. For example, the brain can be stimulated while also obtaining signals, such as MER, PET, EEG, and/or neuro-activation spikes. According to an example embodiment the system is configured to use such signals as a signature with which the VOAs are associated, for the purpose of VOA groupings, similar to that which is described above with respect to using the same therapeutic effect(s) and/or side effect(s). A single brain state can be represented by a combination of signal types. Where a number of VOAs are associated with a selected signal signature, the system is configured to generate a volume by the intersection (or union) of those volumes. For example, the system can generate a plurality of volumes each associated with a different respective MER signal signature. If there is a desired brain state for a patient, the user can enter the relevant brain state, e.g., MER signature, in response to which the system outputs a volume that is based on the VOAs associated with the indicated signal signature. Indeed, over time, doctors/clinicians can come to associate certain biomarkers with desired therapeutic effect, and therefore use such markers for the analysis of the VOAs of the patient population.

In an example embodiment, location-specific data on brain response to respective VOAs, for example as indicated by changes to location-specific biomarkers in the brain, is aggregated over a large number of patients. For treatment of a new patient, the system is configured to obtain biomarkers characterizing a current brain state of the patient. The system is configured to obtain biomarkers representing a desired brain state for the patient. The system is then configured to automatically determine and output a target volume of activation estimated as most likely to achieve the change in brain state from the current brain state to the desired brain state. For this determination, the system is configured to search the library of VOAs and the corresponding aggregated location-specific brain response data to determine which VOA has been shown to produce the response which provide the desired change.

For example, in an example embodiment, information of a new patient, including a corresponding, e.g., novel, indication is entered. A biomarker is found. Brain states are searched. The system then identifies the brain state which would abolish the biomarker. The system then identifies the VOA associated with that brain state, e.g., the VOA which would produce the desired change from the current brain state to produce the identified target brain state. The system then provides that VOA (and associated stimulation settings) as a target volume for treating the entered indication.

6. Filtering VOAs Based on Medications or Time of Day:

The medication a patient is on and the time of day when stimulation is performed can affect stimulation results. According to an example embodiment, the system filters the VOA groupings by the medications which the patient records indicate the patients, to whom the respective VOAs correspond, to have been on at the time of the stimulation. For example, a user can input a medication which a current patient is on, and request a target stimulation volume based on region/voxel combinations of VOAs corresponding to patients on the same medication (and/or dosage). In an example embodiment, the system is configured to consider medication concentration, type, and/or state.

According to an example embodiment, the system filters the VOA groupings by the time of day when the stimulations corresponding to the VOAs were performed. For example, a user can input a time of day (e.g., morning, afternoon, early evening, night), and request a target stimulation volume based on region/voxel combinations of VOAs corresponding to stimulations performed during the relevant time period.

Thus, example embodiments provide for use of a plurality of parameters as filters for analytics. Time or medication concentration/type/state are usable to refine analyses. For example, unfiltered data may show a weak correlation between a particular stimulation volume and an effect, but, upon filtering by time, the data may show a strong correlation between the stimulation volume and the effect when the stimulation is performed in the morning. In an example embodiment, the system is configured to use the filtered analyses to inform future program settings to compensate for changes in time. Similarly, other potential parameters for filtered analyses include, for example, demographics, health state, body position, and/or disease type or subtype.

7. SFM Analysis for Target Volume Generation Based on Selected Clinical Effects:

VOAs can be generated for a plurality of patients of a patient population, and each of all or a subset of the VOAs can be recorded in association with one or more therapeutic effects and/or adverse side effects. In an example embodiment, the system provides a user interface via which a user, e.g., a clinician, can select one or more therapeutic effects, in response to which the system outputs a target volume for achieving the indicated combination of effects based on analysis of the VOAs of the patient population and the therapeutic effects with which they are associated, where only those VOAs which are associated with the indicated therapeutic effects are selected. The system then outputs a volume formed by the overlap of those VOAs or formed of the voxels that are in a significant number of the VOAs associated with that therapeutic effect. In an example embodiment, the system provides a user interface via which the system is configured to receive user input of a threshold number or threshold percentage of considered VOAs in which a voxel must be found to be included in the returned area.

Similarly, according to an example embodiment of the present invention, the system provides a customized side effect volume showing regions to avoid, based on user selected adverse side effects, where the system returns a side effect volume formed by the overlapping of VOAs associated with the indicated side effects, e.g., subtracting therefrom regions in VOAs not associated with the adverse side effects. According to an example embodiment, the user can input both therapeutic effects and adverse side effects to consider, and the system produces a new target volume formed by the overlap of the VOAs associated with the indicated therapeutic effect minus portions associated with the volumes associated with the indicated adverse side effects. Similar to that which is described above, in an example embodiment, the system provides a user interface via which the system is configured to receive user input of a threshold number or threshold percentage of considered side effect VOAs in which a voxel must be found to be considered as belonging to the side effect area.

For example, a user can input a desired primary effect, in response to which the system suggests one or more stimulation target volumes and/or associated stimulation parameters. The user can continually modify and refine the desired effects. For example, the user can input a request for more of a particular clinical effect and/or avoidance of additional side effects, in response to which the system outputs a modified target, until finally the system outputs a suggested final target volume or family of volumes of a circuit.

In an example embodiment, various target effects/structures can be used to guide a trajectory through multiple targets. Select a series of desired effects, and the system, in an example embodiment, shows one or more trajectories through multiple targets that may have disparate results related to the desired effects.

Figure 12:
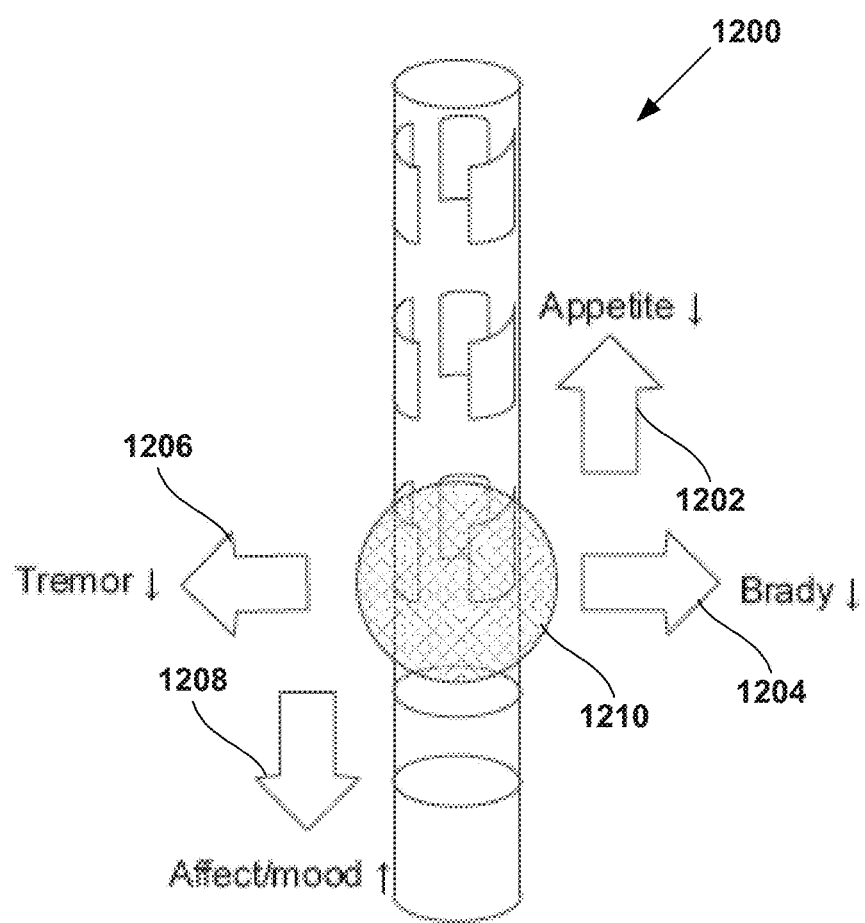
FIG. 12 shows an example of a neighborhood effects map, according to an example embodiment of the present invention.

In an example embodiment of the present invention, a user can input stimulation program settings in response to which the system outputs a display in the graphical user interface (GUI) a map of neighborhood effects showing the respective next change in effects associated with a change in the VOA position, in each of a plurality of directions, from the current VOA position. For example, For example, FIG. 12 shows an example of a neighborhood effects map 1200 with labels 1202, 1204, 1206, 1208 indicating the change in an effect with a change in the VOA 1210 position. In an example embodiment, users can build the neighborhood effects probability atlases, and the users can export, share, and import them.

8. Clinical Effects Analysis for Target Stimulation Time and/or Medication Determination:

According to an example embodiment, the system analyzes the effects of stimulations against time of day to determine a target stimulation time. For example, the system creates a histogram of stimulations by time of day (e.g., morning, afternoon, early evening, night) to determine if a particular therapeutic effect or side effect is statistically significantly associated with a particular time of day, and, if so, outputs such information. This information can differ for different considered therapeutic effect and/or side effects. According to an example embodiment, the system provides an interface in which the user can select combinations of therapeutic effects and/or side effects, and the system determines whether there is a statistically significant time period association for that indicated combination, in which case, the system outputs a recommended time of day for therapy.

Medications taken by respective patients with which the stimulations are associated can be considered in a similar manner to determine a recommending medicinal regimen to follow during the period when stimulation is performed.

The affect that time of day and/or medication has on the clinical effects may be dependent on the particular areas stimulated and/or the demographics of the patients subject to the respective stimulations. Thus, according to an example embodiment, the system tests the statistical significance of time of day and/or medication against different stimulation areas and/or demographics. Thus, different times of day and/or medications can be recommended for different stimulation regions and/or for different patient demographic information.

9. Analysis of VOA Overlap with Target Volume:

According to an example embodiment of the present invention, the system is configured to quantify the extent to which a VOA meets a target volume based on a spatial difference of the VOA and the target volume. For example, the extent to which the VOA extends beyond the target volume, the extent to which the target volume extends beyond the VOA, and the extent to which the VOA and the target volume overlap contribute to an overall score of the VOA. See, for example, U.S. Provisional Patent Application Ser. Nos. 61/521,572, filed Aug. 9, 2011 and 61/549,053, filed Oct. 19, 2011, the entire content of each of which is hereby incorporated by reference herein.

According to an example embodiment of the present invention, the system is configured to determine how well a group of VOAs meets a target volume. For example, the system determines a spatial difference between the group of VOAs and the target volume. For example, the system assigns to each VOA of the group a score indicating how well the respective VOA meets the target, and a combination of the scores can be used as a metric to determine how well the group meets the target volume. For example, a particular set of parameter settings might be common to all of the VOAs of the group, and it may be useful to know the extent to which the settings are expected to produce a VOA that substantially meets the target volume. The score can be used as a metric of the expectation.

Alternatively or additionally, the determination of the extent to which the group of VOAs corresponds to the target volume can be performed for the VOAs as a whole, by which the system calculates a mean and/or standard deviation to rate the VOAs as a group.

According to an example embodiment, the system outputs a number indicating how many or the percentage of the VOAs of the group that meet a certain threshold correspondence with the target volume.

According to an alternative example embodiment, for each point that is included in any of the VOAs of the group, the system determines the number of the VOAs of the group in which the point is included and includes the point in a composite volume if the point is determined to be included in a threshold number or percentage of the VOAs of the group. The system compares the composite volume to the target volume and scores the composite volume based on the degree of similarity between the target and composite volumes. The system outputs the score as a rating of the correspondence between the group of VOAs and the target volume.

According to an example embodiment of the present invention, a similarity of an average center of mass of the group of VOAs and the center of mass of the target volume is a factor used by the system to calculate the rating of the correspondence of the group of VOAs to the target volume.

10. SFM Analysis for Patient-Specific Atlas Generation:

According to an example embodiment of the present invention, the system analyzes VOAs of a plurality of patients to create a new patient population group for obtaining an average atlas to be registered to a new patient, e.g., as described in the '232 application. Clinicians program a leadwire implanted in a patient to obtain certain therapeutic effects, while avoiding adverse side effects as much as possible. Different patients will require different volumes of tissue to be activated for achieving results tailored to that respective patient, because different patients need different therapies and because, even for a same therapy, different patients can require different stimulations for achieving the same desired results. If, despite the tailoring of parameters and VOAs to achieve customized patient-specific results, the VOAs of a group of patients are similar, in an example embodiment, the system forms a new patient population group, which is the group of patients with whom the similar VOAs are associated. For example, in an example embodiment of the present invention, the system compares the VOAs to each other to find significant overlap and/or lack of significant spill. For example, in an example embodiment, for comparison of the VOAs of the patient population to each other, the system uses one or more equations described, for comparing a VOA to a target volume, in U.S. patent application Ser. No. 13/570,736 filed Aug. 9, 2012, which claims priority to U.S. Prov. App. Ser. No. 61/651,282 filed May 24, 2012, 61/549,053 filed Oct. 19, 2011, and 61/521,572 filed Aug. 9, 2011, all of which are incorporated herein by reference in their entireties. Alternatively, the system can use an Overlap Ratio Measure, for example as described in Siegel et al., "Spatiotemporal Dynamics of the Functional Architecture for Gain Fields in Inferior Parietal Lobule of Behaving Monkey," Cerebral Cortex 17(2), pp. 378-390 (February 2007), the contents of which is incorporated by reference herein in its entirety.

In an example embodiment, if the system finds a group of patients within the patient population whose successful VOAs are similar, for example based on the mentioned comparisons, the system generates a new patient population group the members of which are the patients whose corresponding VOAs have been determined to be similar.

In an example embodiment, the new patient population group is used for obtaining a customized atlas for registration to a new patient, e.g., as described in the '232 application. For example, the system determines recorded characteristics, e.g., indication, age, sex, geographic location, medications being taken, etc., of the patients of the new patient population group which are shared by all or a threshold percentage of the new patient population group. If characteristics of a new patient match those characteristics (or a significant number of those characteristics), the system uses an atlas from that new patient population group to register to the new patient, e.g., to a medical image of the new patient. Alternatively, a doctor, surgeon, and/or clinician can view the characteristics associated with various patient population groups and, for example, based on such information, manually select the patient population group to use for obtaining an atlas to register to the new patient. The atlas of the patient population group used for registration to the new patient can be, for example, an average of the atlases of the patient population group, and average medical image of the patient population group (e.g., normalized to a common reference coordinate system), or an atlas generated based on the average image.

According to an example embodiment, the group can be further divided by noted associated therapeutic effect. For example, if of 100 similar VOAs, 50 are associated with a first therapeutic effect and 50 are associated with a second therapeutic effect, then according to an example embodiment, the system generates a first patient population group formed of the patients associated with the first 50 VOAs and generated a second patient population group formed of the patients associated with the second set of 50 VOAs. For atlas registration, the system (or clinician/doctor/surgeon) can select the set associated with the therapeutic effect which is desired to be achieved in the new patient.

According to an example embodiment, the system may similarly form new patient population groups based on similarities in recorded adverse side effect volumes. For example, if VOAs of a plurality of patients which were associated with side effects are recorded, the system is configured to, in an example embodiment, group those patients into a new group, which are then selected for use to create a patient-specific atlas for a new patient, based on similarities between the characteristics of the new patient and that patient population group. As described above, these groupings can be further divided according to type of side effect.

According to an example embodiment of the present invention, the system uses a lack of similarity of VOAs as a factor to determine whether to create a new patient population group. For example, if a group of patients have certain commonalities, e.g., one or more of age, race, geographic location, indication, medications takes, etc., which commonalities would suggest that similar VOAs should be used for those patients, but instead the VOAs for those patients actually break down into two or more groups, where the VOAs in the same one of the groups are similar, but are significantly different than the VOAs in the other groups, then the system forms a new patient population group for each of those groups of VOAs. When an atlas is to be generated for a new patient, in an example embodiment, the system compares an image of the new patient to, for example, average atlases or images of each of the groups, and selects the average atlas or image of the group most similar to the image of the new patient, for registration to the patient for generation of the patient-specific atlas.

Figure 6:
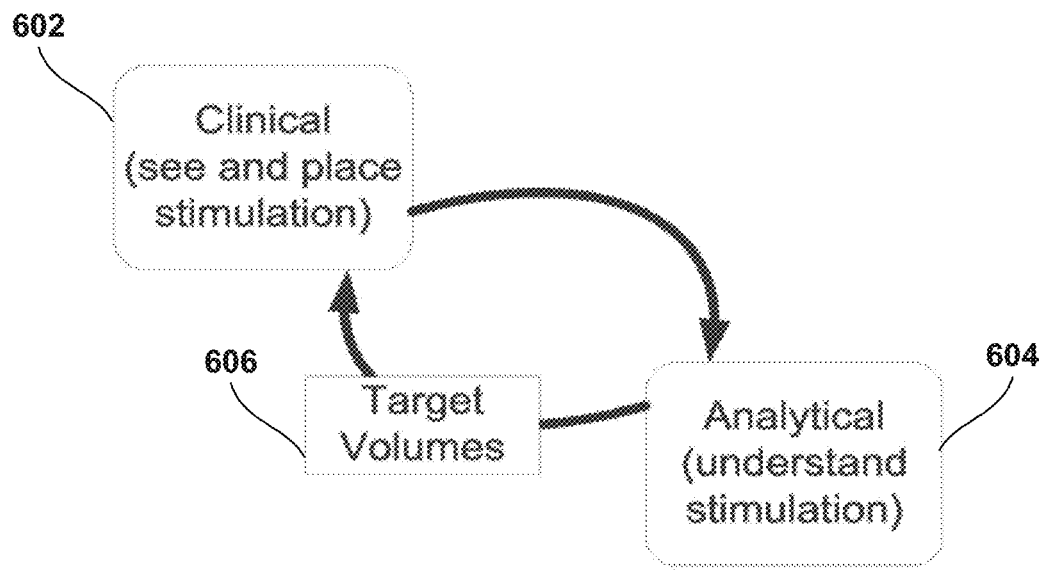
FIG. 6 is a diagram that illustrates a stimulation and analysis cycle by which target volumes and/or stimulation settings can be refined, according to an example embodiment of the present invention.

Thus, as shown in FIG. 6, during a clinical stage 602, a user, e.g., a doctor, patient, clinician, etc. can use a stimulation programming module (or modules) to set stimulation settings to stimulate an anatomical region of a patient. Many users can do this for many patients, e.g., at a same or at a plurality of terminals. The module is configured to generate estimated VOAs corresponding to the stimulation settings. The module is further configured to receive user and/or sensor input regarding clinical effects of the stimulation, which the system stores in association with the respective VOA on a cloud-based data store. The system is further configured to obtain additional patient information, e.g., from an electronic medical file, with which information the VOA is associated. An analysis module 604 performs analyses on the plurality of VOAs, the associated clinical effects, and/or the associated patient information, to refine target and side effect volumes. The user of the programming module can then access the refined target and side effect volumes 606 for tailoring stimulation settings of subsequent stimulations for a plurality of patients. The target and side effect volumes used for the subsequent stimulations can be based on a filtered set of the prior VOAs, e.g., which set is most relevant to the respective patient to whom the subsequent stimulation is being applied. However, aside from use of the VOA analytics to refine target and side effect volumes, in an example embodiment, the system is configured to identify clusters of patients of the patient population based on the respective VOAs associated with respective ones of the patients of the patient population, and identified relationships between such VOAs, where the clusters form respective patient population groups for which respective atlases are provided.

Figure 10:
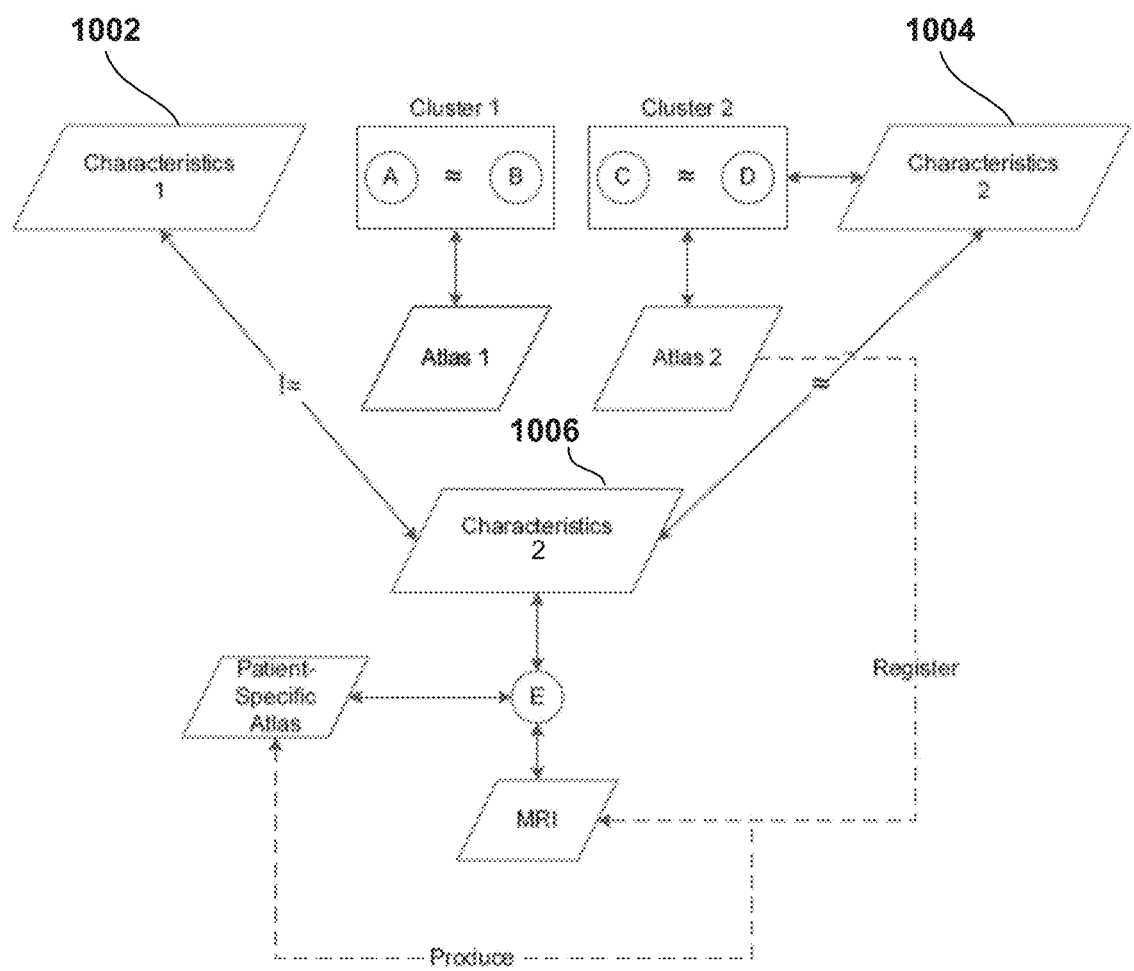
FIG. 10 illustrates generation of a patient-specific atlas based on clustering of sub-sets of a patient population based on clinical effects information associated with VOAs of the patient population, according to an example embodiment of the present invention.

For example, FIG. 10 illustrates an example where the data store includes VOAs corresponding to stimulation programs set for patients A-D, MRIs of the brains of patients A-D, and other medical record information concerning patients A-D. In the illustrated example, the system identified an overlap between the VOAs associated with patients A and B, and identifies an overlap between the VOAs associated with patients C and D. The system therefore generates Cluster 1 formed of patients A and B, and combines data of the MRIs of patients A and B to form Atlas 1 for Cluster 1; and generates Cluster 2 formed of patients C and D, and combines data of the MRIs of patients C and D to form Atlas 2 for Cluster 2. The system also identifies characteristics, e.g., medical record characteristics, shared by patients A and B and characteristics shared by patients C and D, and associates the respective shared characteristics with the respective clusters.

The system is configured to provide user interfaces for stimulation programming and visualization in which the system outputs a graphical representation of an implanted leadwire and/or stimulation volumes, such as estimated VOAs, target volumes, and/or side effect volumes, relative to anatomical structures of the patient, where those anatomical structures are spatially arranged according to a patient-specific anatomical atlas. Therefore, when a new stimulation programming/visualization electronic record for a patient is generated including the patient information used for outputting patient-specific stimulation volume information, the system is configured to store in the electronic record the patient-specific atlas. To do so, in the example illustrated in FIG. 10, the system is configured to select one a plurality of patient population atlases for registration to the new patient. In FIG. 10, the system compares characteristics, e.g., medical record characteristics, which can include, for example, demographics, of new patient E to the respective characteristic sets associated with each of Clusters 1 and 2. In the example shown in FIG. 10, the system has determined that the characteristics of new patient E are most similar to those associated with Cluster 2, and the system therefore selects Atlas 2 of Cluster 2 and registers it to anatomical information, e.g., an Mill of new patient E to generate a patient-specific atlas for patient E.

In an example embodiment, referring to the example illustrated in FIG. 10, subsequent to applying stimulation programs to patient E, patient E can be added to the patient population, and the system is configured to further modify the previously generated clusters in view of VOAs associated with patient E, for example to add patient E to one of the previously generated clusters, to add a new cluster, and/or to break apart one or more previously generated clusters. Thus, the patient population clusters can evolve over time. With each change to the patient population clustering, the system can generate a new respective patient population atlas for each new and/or modified cluster, which the system is configured to use for later generation of patient-specific atlases for newly added patient records. In an example embodiment, the system is configured to update even the patient-specific atlases previously generated for patients, e.g., even ones previously included in a cluster, based on a modification to the patient population clusterings.

11. Patient-Specific Atlas Generation Based on a Hierarchy of Images or Atlases of a Patient Population:

According to an example embodiment of the present invention, take the Mill of many patients and either using the whole Mill or regions of interest within it (e.g., Basal Ganglia), cluster the images (or corresponding atlases) using some metric of image similarity, e.g., to create a hierarchy of medical images or atlases. For example, the clustering of the database images may be done hierarchically so as to obtain a cluster tree, where, at the bottom of the tree, the individual images are the leaf nodes, which can then branch upward to a node of a higher hierarchical level. The nodes of the higher hierarchical levels correspond to a template constructed based on the images/templates of nodes of the branches below the respective node.

In an example embodiment, the hierarchical tree is used for efficiently finding an image/atlas to register to a new patient. For example, the system compares an image of a new patient to the average image/atlas of the nodes beginning with the top hierarchical level, working downwards until branch by branch, at each level selecting the node with the greatest match, until selecting the best leaf node. In this manner, the new patient's image need not be compared to each leaf node to find the best match. The selected leaf node's atlas can then be registered to the image of the new patient to form the patient-specific atlas. This may enable an efficient search for similarity between the patient and the candidates.

In an example embodiment, the system selects from the hierarchy the 'n' closest MRIs transformed to a common space, e.g., Montreal Neurological Institute (MNI) space and/or takes the average MRI (or other mathematically constructed MRI combination) that best represents the 'n' Mills, and the system registers the selected MRI/Atlas for registration to the new patient's medical image.

12. Interface for User Input of Logical Combinations of SFMs for Target and/or Side Effect Volume Generation:

According to an example embodiment, the system provides a user interface by which the user can select characteristics to consider when generating a target and/or adverse side effect volume, and to also select a logical operator to use for the generation of the new volume. For example, the user can input an instruction to a return a new volume based on all therapeutic VOAs associated with one or more therapeutic effects and/or one or more identified patient characteristics with which the VOAs are associated, and further select an operator such as union or intersect. For example, the user can select a union of VOAs of a certain type, in response to which the system returns a volume composed of the combination of areas in the relevant VOAs, or the user can select an intersection of volumes, in response to which the system returns a volume composed of the areas found in all (or a threshold percentage) of the relevant VOAs. Another logical operation can be NOT, where the user can indicate certain VOAs not to be considered (for example not VOAs associated with particular specified patients, not patients of particular specified doctors, and/or not patients of a certain demographic, etc.; and/or the reverse, only VOAs associated with particular specified patients, only patients of particular specified doctors, and/or only patients of a certain demographic, etc.) or where the user can indicate areas to be removed, e.g., remove from the union or intersection those areas that are also found in VOAs associated with certain specified adverse side effects. The user can similarly select to have a side effect volume returned, formed by the combination (e.g., union or intersection, as specified) of VOAs associated with certain specified adverse side effects.

According to an example embodiment, the system further allows input of multiple logical operators such as a combination of both union and intersection. For example, the user can input an instruction to return a volume formed of the intersection of (a) a first group of one or more VOAs with (b) the union of VOAs of a second group, in response to which the system would find the area formed by the union of the second group, and find the area formed by the intersection of that union area with the area within the VOAs of the first group.

Thus, the system provides a user interface which includes a toolset by which a user can define how the system generates new volumes which the user can then use, e.g., for a current patient, for example, to set stimulation parameters of a current patient.

13. Other Analyses:

SFM analyses can include analysis of variance (ANOVA), generalized linear models, parametric or non-parametric techniques, Bayesian analysis, etc.

Obtaining Analysis Paradigms and/or Data for Analysis

According to an example embodiment of the present invention, the system includes features by which to collect VOA related data over time to then be subject to an analysis, for example, one or more of the analyses described above. According to an example embodiment, the system is configured such that, where a user begins compilation of a parameter set of an analysis to be conducted on an input set of data, e.g., an input set of VOAs, as described above, the user is able to save the constructed analysis paradigm and retrieve it a later time, e.g., for modification and/or application to a set of data input. In an example embodiment, a saved analysis paradigm may function as a template, e.g., which can be copied as a new analysis paradigm, which copy can be further modified. Moreover, the data collection to which an analysis is applied can be a parameter of a saved analysis paradigm. A template can be copied multiple times, and modified to be applied to different sets of data.

In an example embodiment, an analysis template can be saved without specification of a data collection to which the analysis is to be applied. Such a template can be copied as a new analysis record and modified to specify the data collection on which the analysis is performed and to include results of such an analysis. Multiple copies can be saved, each specifying, for example, a different data collection.

For example, an analysis paradigm can be set up by which to find spatial differences between two different types of groups, Group A data set and Group B data set. Further, the analysis can be set with, for example, certain thresholds to rate the data (e.g., threshold overlap or threshold difference), certain statistical tests to be applied, etc. Thus, there can be a number of parameters to use for an analysis. Such a paradigm specifying one or more of such variable parameters can be saved as a template, and copied as new analysis paradigms to which to apply different data sets or modified analysis parameters, for which a user can select an activation instruction, in response to which the system runs the modified analysis on the respectively specified data. For example, the system may display a "run" button in a GUI, in response to selection of which, the system runs the specified analysis.

According to an example embodiment, the templates can be stored as a data structure that can be shared by users. For example, in an example embodiment, a template can be attached to an e-mail which one user can send to another user, which other user can open and modify or otherwise use the attached template, e.g., where the other user also includes the software adapted to interpret the data structure. Alternatively or additionally, the template can be stored in a central location accessible by a plurality of terminals on which the software is run. In an example embodiment, the data collection, e.g. VOAs and/or associated stimulation parameters, to which the analysis is applied can also be shared e.g., separate from the template and/or as part of the template.

According to an example embodiment of the present invention, the system is configured for storing associated groups of data, e.g., groups of VOAs and/or associated stimulation parameter sets, which groups can be opened by a user to be subjected to various analyses. The groups can further be modified over time. For example, in an example embodiment, the system includes an interface, e.g., a graphical user interface and/or other interface, via which to receive user input for specifying a set of stimulation parameters and/or associated VOAs, and/or via which to output the set of stimulation parameters and/or graphical representations of such VOAs. The system further includes, according to an example embodiment, a selectable menu item, such as an option of a "File" menu selectable from a toolbar, which, when selected allows the user to save the presently open stimulation settings and/or VOA to a database folder representing the group. If no folder representing the group has been previously set up, or if the user otherwise wants a new group, the system allows the user to select "New Folder" or "New Group" or the like to create the folder/group with which to associate the open settings and/or VOA.

In an example embodiment of the present invention, the system displays in a GUI selectable graphical representations of groups that have been previously created, provided for user selection to associate a set of stimulation parameters and/or a VOA that is in focus with the selected group representation. In an example embodiment, the set of settings and/or VOA can be added by drag-and-drop. For example, an icon representing the set of settings and/or VOA that is in focus, e.g., that is displayed, is selectable and can be dropped onto one of the group representations to be included as part of the group. Each stored group can be separately subjected to one or more analyses. In an example embodiment, the system also includes an icon for creating a new group, which is selectable and/or to which a set of stimulation settings and/or a VOA can be dropped, in response to which selection or drop, the system provides for a user interaction by which to name a new group to which the set of settings and/or VOA that is in focus can be added.

For example, as a clinician notices various symptoms associated with a particular VOA, the clinician can use the GUI features to drop the VOA into various "buckets" that can later be used for analysis. For example, the clinician notices eye movement, and therefore associates the VOA in focus with a bucket of VOAs that resulted in eye movement. In this regard, a VOA and/or a set of stimulation settings can be associated with more than one data group, and can be subjected to analyses of such different groups and/or subject to different types of analyses. At any point in time, a user can use the system to subject such a bucket to an analysis, during which the system performs an analysis, e.g., as described herein, on those volumes that are included in the bucket. It is noted that the system can similarly maintain buckets of side effect volumes and target volumes on which analyses can be run.

Various kinds of data can be associated with VOAs (or other volumes), by which the VOAs (or other volumes) can be filtered. Such data can include, for example, diagnosis, age, gender, medication used, clinical test scores, patient assessment of well being, target volume with which the VOA and/or stimulation settings are associated, variance of a medical image of a patient with which the VOA and/or stimulation settings are associated from a standard atlas, quantitative data from a measurement device such as an accelerometer, of a sensor whose signals can have a certain significance, e.g., indicating tremor, straightness of lines, dwell time, etc. According to an example embodiment, a user can filter stored VOAs (or other volume types) and/or sets of stimulation settings by such data, and apply the filtered group to an analysis. For example, with respect to variance between medical image and standard atlas, a user might want to filter out those VOAs and/or settings that are associated with a patient whose medical image(s) varies from a standard atlas by a threshold amount, since results of a stimulation applied to such a patient may be expected to be different than those normally expected from a patient whose anatomy more closely corresponds to the typical anatomical arrangement. Aside from entering filter parameters for obtaining a matching set of volumes to be immediately subjected to an analysis, the system is also configured to provide for filtering of the volumes to obtain a filtered set that can be stored as a new bucket, which can later be retrieved, e.g., for running one or more analyses.

Creation and Sharing of Target Volumes

According to an example embodiment of the present invention, a system is provided that provides for a cycle of testing stimulation settings that produce corresponding VOAs, obtaining results of such tested settings, analyzing such results, selecting a refined target volume based on such analyses, and selecting new stimulation settings to be tested. A refined volume can be selected, e.g., by changing the volume's position, orientation, size, shape, etc. Moreover, in an example embodiment, such modifications can be performed graphically, e.g., by manipulation of graphically displayed nodes.

This cycle can be repeated, e.g., continuously, to refine the stimulation settings. Moreover, the testing can be of stimulation settings of a plurality of patients and the analyses can be of results of such tested settings and/or their corresponding VOAs of a plurality of patients.

For example, information concerning such settings, their corresponding VOAs, and respective results of stimulations using such settings can be stored at a single location for access by one or more clinicians who can set new target volumes and/or choose modified target stimulation regions based on results of the analyses. FIG. 6 illustrates the stimulation and analysis cycle by which target volumes and/or stimulation settings can be refined.

Figure 7:
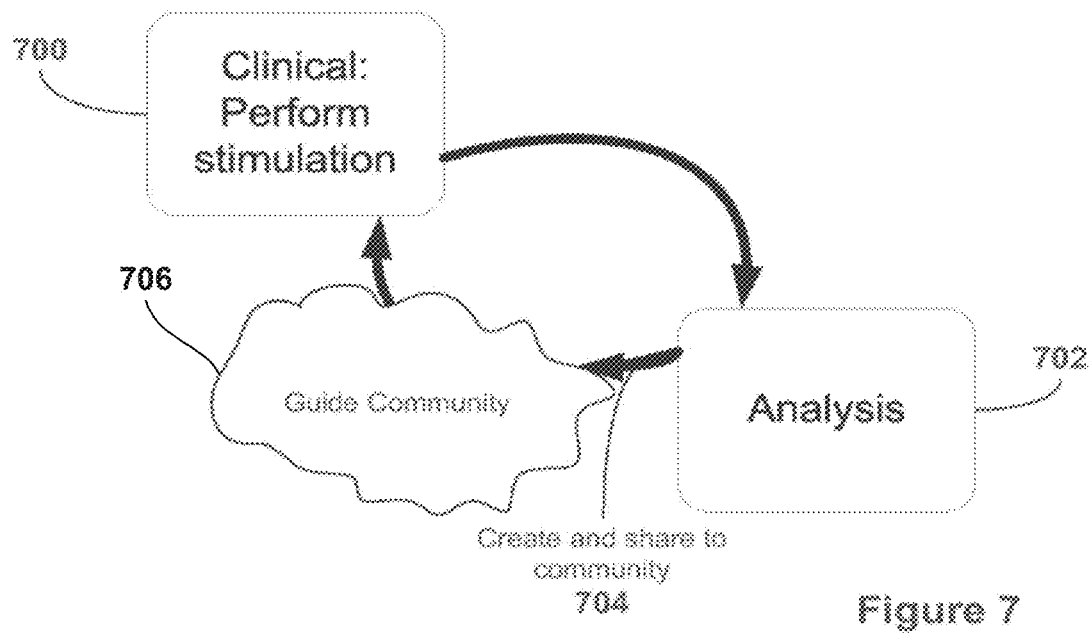
FIG. 7 is a diagram that illustrates a stimulation and analysis cycle with volume sharing, according to an example embodiment of the present invention.

FIG. 7 shows a modified cycle according to an example embodiment of the present invention, according to which users are able to share and/or publish their discovered and/or input target volumes for implementation by other users. For example, at a step 700, a guide module can transmit stimulation settings to an IPG for application of those settings to electrodes of an implanted leadwire to stimulate an anatomical region of a patient. At step 702 an analysis can be performed on the tested settings, corresponding VOAs, and/or results of such stimulations, tested by one or more clinicians on one or more patients. At step 704, a user can select a new target region based on the analysis, and share it with a community 706 of users, e.g., clinicians, researchers, and/or other users, who can use such a shared target region to select new stimulation settings to test at 700.

Figure 8:
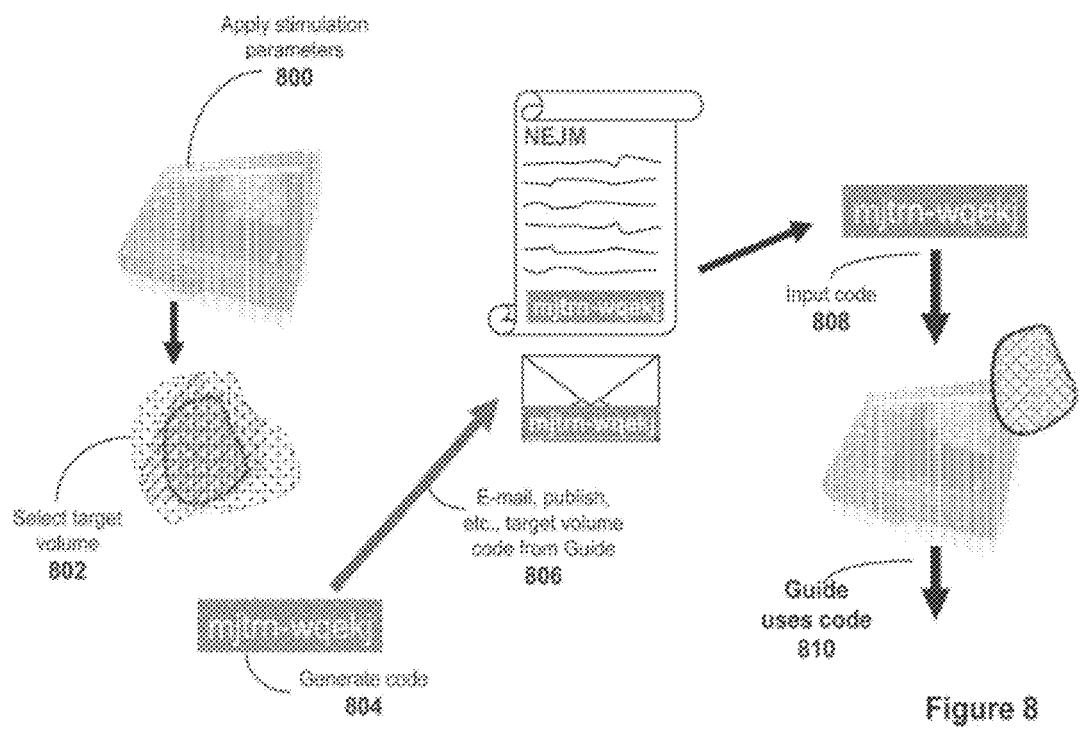
FIG. 8 illustrates a data flow including volume sharing, according to an example embodiment of the present invention.

Referring to FIG. 8, according to an example embodiment, at step 800, a first doctor, "Dr. A," uses a Guide module on a workstation, to set stimulation parameters, view a corresponding VOA, apply the settings to an IPG and an implanted electrode leadwire, and/or record results of such stimulation settings.

At step 802, Dr. A selects a target volume based on the results of the applied stimulation settings. (It is noted that a different doctor may instead select the volume. It is also noted that the newly selected volume can be based on analysis of results of settings applied to more than one patient by more than one doctor. It is also noted that the selection of the new target volume can be further based on results of a plurality of different applied sets of stimulation settings. It is also noted that the analysis can be manual or can be automatic, e.g., using one or more of the analyses described above.)

At step 804, the Guide module generates a code for the target volume set by Dr. A. For example, Dr. A selects an option to save the input target volume and the system responsively generates and outputs a code associated with the saved target volume. For example, Dr. A can save the target volume under any descriptive name by which Dr. A can later identify the target volume in a useful manner, but the system can store a field, that includes the generated code, in association with the saved target volume. Further, in an example embodiment, the field can be opened for view by Dr. A so that Dr. A can later identify the code if otherwise forgotten. For example, in an example embodiment, responsive to right-clicking a representation of a file corresponding to the target volume, the user is able to view properties of the file, including the generated code. Alternatively, when the target volume is opened by Dr. A, the system also displays the code. (In an alternative example embodiment, the doctor manually enters a code, and the system is configured to inform the doctor whether the entered code is available.)

At step 806, Dr. A shares the code with one or more other doctors. For example, Dr. A e-mails the code or otherwise publishes the code. At step 808, Dr. B inputs the code into an instantiated Guide module running on Dr. B's terminal, in response to which, at step 810, the Guide module into which Dr. B input the code displays or otherwise uses the target volume selected by Dr. A and for which the code was previously generated. For example, in an example embodiment target volumes are accessible via an alphanumeric code that is published so that other users can then use the code to access a central server that provides them with the target volume, e.g., they can be downloaded via a webpage of the cloud.

In an example embodiment, when other users import such published volumes, the system provides for the importing user to tag the imported volume, for example, with data identifying who generated the volume, in which facility the data was generated, etc., and to store the tagged volume in a folder owned by the importing user. In an alternative embodiment, the system is configured to automatically append such metadata, e.g., which can be accessed by the importing user.

The target volume selected at step 802 can be generated manually by Dr. A, e.g., by manipulation of graphical nodes in a user interface, or can be generated automatically by the system based on input, e.g., selected by Dr. A. For example, Dr. A can input a group including a plurality of sets of stimulations settings, corresponding VOAs, and results into a system-run analysis, e.g., one of the analyses described above, based on target generation parameters (pre-programmed and/or user input) of which the system outputs the target volume, which Dr. A can select for saving.

Dr. A can store a plurality of target volumes. For example, different ones of the stored target volumes can be associated with different groups of patients. For example, different target volumes can be associated with different desired therapeutic effects, different diseases, different indications, etc. In an example embodiment, the system enables the user to identify the characteristic with which the target volume is to be associated. For example, a file name or folder name can be used to identify the characteristic.

While the above discussion concerning sharing of volumes, e.g., in connection with FIG. 8, has been described with respect to target volumes, in an example embodiment, the system also provides for a user to likewise share side effect volumes. For example, Dr. A can manually enter a side effect region where stimulation is to be avoided or the system can automatically generate a side effect region, e.g., as described above in the "Group Comparisons" section. The system can assign a code to the side effect region, which code can be shared as described above with respect to the target volumes.

In an example embodiment of the present invention, the system stores the user-defined/selected target and/or side effect regions at a central location accessible by a plurality of terminals running a Guide module. It is noted that a number of users can also use a single terminal using different log-in information. The different users of the same or different terminals can thereby obtain, from the central location and via a network, e.g., the Internet, the stored target and/or side effect region previously selected by a different user. The user can identify which volume to obtain by entering the corresponding code.

In an alternative example embodiment, the system generates a code for the selected target or side effect volume based on characteristics of the volume. In an example embodiment, the generation of the code based on the characteristics of the volume is such that the system is able to reconstruct the volume based on the code. For example, the code may be based on one or more of a center of mass of the volume and spatial coordinates of a perimeter of the volume. Other characteristics of the volume as described above with respect to data stored to represent a volume can additionally or alternatively be used. Accordingly, the volume need not be stored. Instead, a user can share a selected volume by sharing the code generated by the system, and another user can enter the shared code, in response to which the system outputs the volume reconstructed based on the code.

In an example embodiment, when a first user, using the Guide software to program a system, enters a code to open a volume shared by a second user, the system is configured to modify the shared volume to reflect an anatomy of the patient. For example, the shared volume might have been generated in a space corresponding to the brain of a different patient or in a generic atlas space, which varies from the anatomical space corresponding to the brain of the currently active patient information.

In an alternative example embodiment the system initially opens the volume according to the spatial environment in which it is saved or according to a generic atlas space (even if the volume was generated in relation to an anatomical space of another patient), and subsequently, in response to a user conversion instruction, transforms the volume to reflect the anatomy of a currently active patient. According to the embodiment in which the code is automatically generated based on characteristics of the volume, in an example embodiment the system is configured to, when a user selects to open the shared volume, open the volume in a generic atlas space, and the user can instruct the system to convert the volume to the patient anatomical space.

The volume being shared can be stored by the system in a manner by which it is not associated with any patient for whom the shared volume was created, in order to preserve the patient's privacy. For example, as noted above, even if the volume is generated in relation to an anatomical space of a patient, the system can be configured to output the shared volume transformed to a generic atlas space. Alternatively, the patient-specific anatomical space can be output since it cannot be used to easily identify the patient.

The system thus facilitates a continuous cycle of refinement of volumes. For example, a first clinician can open a number of target volumes selected by one or more other clinicians based, for example, on similar findings reported by the one or more other clinicians. The user can then have the system run an analysis to find overlapping regions of the multiple target volumes, as discussed above, to thereby form a further refined target volume.

In an example embodiment of the present invention, the system further includes an option to automatically generate a target volume based on a combination of VOAs that correspond to the multiple selected target volumes. For example, in response to receipt of user input selecting the option to generate the target volume based on the underlying VOAs, the system is configured to find for each of the selected target volumes a best fit set of stimulation variables to provide a respective best fit VOA. The best fit parameter settings and VOA can be patient-specific to a currently active or selected patient. The system then performs the analysis upon the plurality of VOAs to find a new target volume (for which the system is configured to also find a further set of best fit parameter settings and corresponding VOA).

Alternatively, the user can have the system graphically overlap the multiple selected target volumes of the one or more other clinicians or the corresponding best VOAs, and manually outline a new target volume based on the displayed overlap.

Web Forum

According to an example embodiment of the present invention, the system includes a server to which system users' volumes are uploaded. A user can create a new web group maintained by the server and invite/add other users to the user-hosted group. Those other users who accept/join the group are then able to view and use volumes shared with the group by other members of the group.

Target Volume Creation (Moving Results to Clinic)

Analysis results can be used to generate target (visualization) volumes for both benefits and side-effects. Target volumes can be saved as a mesh or a point (e.g., a centroid with additional information as described above).

In an example embodiment, a target volume is definable by a selected point about which the volume is to be drawn and a volume size. (Angles can further be used to define an orientation of the target volume relative to axes of an anatomical space.) For example, in an example embodiment, the system is configured to identify an average center of mass of a selected plurality of VOAs. For example, the system is configured to provide a user-selectable option, in response to selection of which the system is configured to calculate the average center of mass of a set of VOAs selected by the user. The system is further configured to receive a size information and draw a target volume centered on the calculated average center of mass and that is of the size specified by the user.

In an alternative example embodiment, or as an additional alternative option, instead of an average center of mass of the VOAs, the system finds a respective average score for each of a plurality of voxels, where the average score for a voxel is an average of the scores of the VOAs in which the respective voxel is included. The score of a VOA can be based on, for example, results of a stimulation to which the VOA corresponds, as described above. In an example embodiment, the system selects the voxel having the highest average score as the point about which to draw the target volume. Alternatively, the system finds a cluster of highest average scoring voxels, and selects the center of such a cluster as the point about which to draw the target volume. The user can manually enter a size, which the user might determine based on a general intuitive feel.

In an alternative example embodiment, or as an additional alternative option, the system first removes from consideration those VOAs having a score below a predetermined programmed threshold, or a threshold specified by the user, and then finds the voxel having the highest average score (or center of a cluster of highest scoring voxels) of the remaining VOAs to set as the point about which to draw the target volume.

In an alternative example embodiment, or as an additional alternative option, the system first removes from consideration those VOAs having a score below a predetermined programmed threshold, or a threshold specified by the user, and then finds the average center of mass of the remaining VOAs to set as the point about which to draw the target volume.

In an alternative example embodiment of the present invention, the system is configured to receive user input of a target volume size (e.g., as number of voxels, a radius, or any other suitable specification of size), in accordance with which size specification the system is configured to adjust a score threshold to one that results in removing just enough voxels to provide a volume approximately equal to the specified size. Alternatively, the system is configured to receive user input of a target volume size (e.g., as number of voxels, a radius, or any other suitable specification of size), in accordance with which size specification the system is configured to adjust a score threshold to one that results in removing just enough voxels to ensure that the specified size is not exceeded. Alternatively, the system is configured to receive user input of a target volume size (e.g., as number of voxels, a radius, or any other suitable specification of size), in accordance with which size specification the system is configured to adjust a score threshold to one that results in removing just enough voxels to ensure that the specified size is not undershot. In an example embodiment, these described methods of adjusting a threshold in accordance with a user-specified volume size are provided as user-selectable options.

The threshold value can be a percentage, e.g., a user may require the target volume to encompass voxels that make up 80% of all the scores of the considered voxels. For example, the system is configured to receive user-input specifying a percentage, and to set the threshold such that the combined average scores of the remaining voxels (whose individual average scores meet the threshold) is equal to the specified percentage of the sum of the average scores of all considered voxels. That is, the voxels of the output volume are such that $$\frac{\sum_{i=1}^{n\_output} avg\_score\_of\_voxel_i}{\sum_{j=1}^{n\_input} avg\_score\_of\_voxel_j} = x\%,$$

where i is a voxel of the output volume, n_output is the number voxels in the output volume, j is a voxel of one or more of the input volumes, n_input is the number of voxels that are included in at least one of the input volumes, and x is the percentage specified by the user.

Compatibility

In an example embodiment, the system is configured to provide compatibility modes in which to generate and/or analyze VOAs. The system is configured to provide de-featuring in the compatibility modes. For example, data can be scaled down to render the data compatible with third party analysis tools, to allow users to perform analysis from the perspective of the other systems.

In an example compatibility mode, the system turns off the ability to simulate VOAs using multiple independent current or voltage sources, so that only a single source is used for all contacts.

After turning off the relevant features, VOAs can then be generated as if they were done using the hardware and parameters supported by the other systems. Such VOAs can then be applied to a visualization, programming, or analysis tool.

As another example, certain systems allows for leadwire contacts to each be set to either on or off, while other systems allow for leadwire contacts to each be set to a plurality of levels besides for on and off, e.g., 20% power, 30% power, etc. If a user is using a system of the former type, the user can set the Guide and/or analysis modules to a compatibility mode in which contact settings can be set to only on and off, and to lockout features not supported by the used hardware. In an example embodiment, the user is presented with a checklist of features for each of which the user can input whether the feature is supported by the hardware being used.

Additional Feature:

Preop:

Using the Target and Side Effect regions, and additional constraints, automatically compute an optimal trajectory for implant.

Take the MRI of a plurality of patients and either using the whole MRI or regions of interest within it (e.g., Basal Ganglia), cluster the images using a metric of image similarity. For generating a customized atlas for a new patient, examine to which patients in the database the patient is most similar. The system creates an atlas template for use in the new patient's surgery based in the 'n' closest database MRIs. The atlas can be created by transforming the 'n' closest MRIs to a standard space, e.g., MNI space or it may be created by finding an "average MRI" that best represents the 'n' database MRIs. This may be accomplished using a variety of non-linear registration algorithms. The clustering of the database images can be done hierarchically so as to obtain a cluster tree. At the bottom of the tree are the individual images, and at each branch the system can construct a template utilizing the images below it. This enables an efficient search for similarity between the patient and the candidates.

Postop:

Aggregate VOAs across subjects using a standard space (e.g., MNI space) or within a new space which is the space of the average MRI that best represents this subjects MRI.

Enable analytics by allowing clinicians to do "set theory" on the VOAs. For example, clinicians can compute voxels that are common to 1, 2, 3, . . . VOAs in the database. Each voxel is tagged by all the behavioral scores that its stimulation led to. For example, stimulation of a voxel in one patient may lead to low tremor, in another patient stimulation of the same voxel may lead to high tremor. Physicians can export this data, associating voxels with scores offline for their own analysis, but they can also use the system to do analysis on the information.

For example, users can identify voxels whose activation significantly affects the stimulation using the following method. The system obtains for each voxel a series of scores, in the off (not activated) and on (activated) states. The system determines the difference between average scores during the on and off states. The system permutes the on and off scores randomly and recomputes the difference. This is done 10,000 or so times, and the system plots a histogram of the scores to see where the original difference sits in this histogram. The histogram is the null distribution. If the voxel influences the score significantly, the real difference should be in the tail of the histogram. Definition of the tail requires a threshold, also known as a 'p' value. In an example embodiment, the system provides a user interface by which to specify this threshold (e.g., 0.05, 0.1, etc.) which means that 5% of the values in the null distribution exceed this threshold or 10% exceed this threshold, respectively. The system can display either the voxels that are in the tail according to a user specified threshold or the system can output to the user the 'p' value map itself as a false color 3D map. For example, in an example embodiment, the latter is displayed as false color slices through a 3D space, for example overlayed on the MRI. Other statistical methods can be alternatively used.

According to an example embodiment, the system obtains the activating function in the direction in which it is maximum at each voxel as an independent variable and the behavioral score as an independent variable and determines which voxels show the most robust correlation between the behavioral scores and the activating function magnitude. There are some voxels for which high values of the activating function lead to negative values of the scores relative to baseline (symptoms improve), some voxels for which high values of the activating function lead to positive values relative to baseline (symptoms worsen), and finally some voxels for which the activating function and the symptom improvement are independent of each other. Thus, the system, according to this example embodiment, uses the correlation of the activating function and the scores to determine the effect of voxels on the considered clinical effect.

According to an example embodiment, for each stimulus setting, the electric field distribution and the corresponding activation can be computed using simplified models. If activation of a given region is desired while avoiding affecting another region, an objective function is used that maximizes the overlap with the region of desired activation and minimizes the overlap with the other region. Many objective functions can be used. A difference of the overlaps may be the most efficient. A search in parameter space can be performed to minimize the objective function. Multiple search strategies are possible.

According to an example embodiment of the present invention, a large database of lead contact positions, stimulus parameters, and outcomes are obtained and the system performs a machine learning exercise to model the dependence of stimulus parameters on the outcomes and the contact positions.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. The methods described herein can be performed using any type of processor or any combination of processors where each processor performs at least part of the process. Systems referenced herein typically include memory and typically include methods for communication with other devices including mobile devices. Methods of communication can include both wired and wireless (e.g., RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

The methods disclosed herein can be implemented by computer program instructions. These program instructions may be provided to a processor to produce a machine, such that the instructions, which execute on the processor, create means for implementing the actions. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated.

The above description is intended to be illustrative, and not restrictive. Those skilled in the art can appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and the following claims.

What is claimed is:

1. A computer-implemented method, comprising:
    obtaining a plurality of estimated volumes of activation (VOAs) associated with electrical stimulations of a patient population;
    obtaining one or more clinical indications or one or more therapeutic effects for each of the estimated VOAs;
    determining a recommended VOA using the estimated VOAs and the one or more clinical indications or the one or more therapeutic effects of the estimated VOAs;
    providing a user interface with a first input element for inputting a first degree upon which a recommendation of a VOA depends on obtaining a specified one of the one or more therapeutic effects;
    upon receiving an input from the first input element, determining a new recommended VOA using the first degree, the estimated VOAs, and the one or more clinical indications or the one or more therapeutic effects of the estimated VOAs; and
    outputting a set of stimulation parameters associated with the new recommended VOA.

2. The computer-implemented method of claim 1, further comprising obtaining one or more side effects;
    wherein determining the recommended VOA comprises determining a recommended VOA using the estimated VOAs, the one or more side effects, and the one or more clinical indications or the one or more therapeutic effects.

3. The computer-implemented method of claim 2, further comprising
    providing the user interface with a second input element for inputting a second degree upon which a recommendation of a VOA depends on avoiding a specified one of the one or more side effects;
    wherein determining the new recommended VOA comprises, upon receiving an input from the second input element, determining the new recommended VOA using the first degree, the second degree, the one or more side effects, the estimated VOAs, and the one or more clinical indications or the one or more therapeutic effects.

4. The computer-implemented method of claim 3, wherein determining the new recommended VOA comprises determining the new recommended VOA using the first degree, the second degree, the estimated VOAs, and the one or more clinical indications or the one or more therapeutic effects, as well as a requirement of no increase in the one or more side effects.

5. The computer-implemented method of claim 3, wherein determining the new recommended VOA comprises determining the new recommended VOA using the first degree, the second degree, the estimated VOAs, and the one or more clinical indications or the one or more therapeutic effects, as well as a requirement of a smallest increase in the one or more side effects.

6. The method of claim 2, wherein obtaining the one or more side effects comprises obtaining a degree of severity for each of the one or more side effects.

7. The method of claim 6, wherein determining the recommended VOA comprises determining a recommended VOA using the estimated VOAs, the one or more side effects, the degree of severity for each of the one or more side effects, and the one or more clinical indications or the one or more therapeutic effects.

8. The computer-implemented method of claim 1, further comprising determining a trajectory of VOAs between the recommended VOA and the new recommended VOA and outputting an indication of the trajectory.

9. The computer-implemented method of claim 8, further comprising outputting an indication when one or more VOAs along the trajectory are associated with causing adverse side effects.

10. The computer-implemented method of claim 8, wherein determining the trajectory comprises determining multiple trajectories and selecting one of the multiple trajectories based on avoidance of side effects.

11. The computer-implemented method of claim 8, wherein determining the trajectory comprises determining multiple trajectories and selecting one of the multiple trajectories based on fewer VOAs along the trajectory with adverse side effects.

12. A system, comprising:
a display screen;
a memory device having program instructions stored thereon; and
a processor coupled to the display screen and configured for executing the program instructions, wherein the program instructions comprise:
obtaining a plurality of estimated volumes of activation (VOAs) associated with electrical stimulations of a patient population;
obtaining one or more clinical indications or one or more therapeutic effects for each of the estimated VOAs;
determining a recommended VOA using the estimated VOAs and the one or more clinical indications or the one or more therapeutic effects of the estimated VOAs;
providing a user interface with a first input element for inputting a first degree upon which a recommendation of a VOA depends on obtaining a specified one of the one or more therapeutic effects;
upon receiving an input from the first input element, determining a new recommended VOA using the first degree, the estimated VOAs, and the one or more clinical indications or the one or more therapeutic effects of the estimated VOAs; and
outputting a set of stimulation parameters associated with the new recommended VOA.

13. The system of claim 12, wherein the processor is further configured for obtaining one or more side effects;
wherein determining the recommended VOA comprises determining a recommended VOA using the estimated VOAs, the one or more side effects, and the one or more clinical indications or the one or more therapeutic effects.

14. The system of claim 13, wherein the processor is further configured for
providing the user interface with a second input element for inputting a second degree upon which a recommendation of a VOA depends on avoiding a specified one of the one or more side effects;
wherein determining the new recommended VOA comprises, upon receiving an input from the second input element, determining the new recommended VOA using the first degree, the second degree, the one or more side effects, the estimated VOAs, and the one or more clinical indications or the one or more therapeutic effects.

15. The system of claim 14, wherein determining the new recommended VOA comprises determining the new recommended VOA using the first degree, the second degree, the estimated VOAs, and the one or more clinical indications or the one or more therapeutic effects, as well as a requirement of no increase in the one or more side effects.

16. The system of claim 14, wherein determining the new recommended VOA comprises determining the new recommended VOA using the first degree, the second degree, the estimated VOAs, and the one or more clinical indications or the one or more therapeutic effects, as well as a requirement of a smallest increase in the one or more side effects.

17. The system of claim 12, wherein the processor is further configured for determining a trajectory of VOAs between the recommended VOA and the new recommended VOA and outputting an indication of the trajectory.

18. The system of claim 12, wherein the processor is further configured for outputting an indication when one or more VOAs along the trajectory are associated with causing adverse side effects.

19. The system of claim 12, wherein determining the trajectory comprises determining multiple trajectories and selecting one of the multiple trajectories based on avoidance of side effects.

20. The system of claim 12, wherein determining the trajectory comprises determining multiple trajectories and selecting one of the multiple trajectories based on fewer VOAs along the trajectory with adverse side effects.

* * * * *